(12) United States Patent
Murray et al.

(10) Patent No.: US 11,094,518 B2
(45) Date of Patent: Aug. 17, 2021

(54) DEVICES AND METHODS FOR DEEP UV LASER ABLATION

(71) Applicant: Board of Supervisors of Louisiana State University and Agricultural and Mechanical College, Baton Rouge, LA (US)

(72) Inventors: Kermit King Murray, Baton Rouge, LA (US); Fabrizio Donnarumma, Baton Rouge, LA (US); Oluwaremilekun Lawai, Baton Rouge, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 0 days.

(21) Appl. No.: 16/891,142

(22) Filed: Jun. 3, 2020

(65) Prior Publication Data
US 2020/0381235 A1   Dec. 3, 2020

Related U.S. Application Data

(60) Provisional application No. 62/856,710, filed on Jun. 3, 2019.

(51) Int. Cl.
*H01J 49/04*   (2006.01)
*H01J 49/40*   (2006.01)
(Continued)

(52) U.S. Cl.
CPC ...... *H01J 49/0463* (2013.01); *B23K 26/0006* (2013.01); *B23K 26/127* (2013.01); *B23K 26/16* (2013.01); *G01N 33/4833* (2013.01); *G01N 33/49* (2013.01); *H01J 49/0031* (2013.01); *H01J 49/0404* (2013.01); *H01J 49/0418* (2013.01); *H01J 49/0445* (2013.01); *H01J 49/164* (2013.01); *H01J 49/165* (2013.01);
(Continued)

(58) Field of Classification Search
CPC ...... H01J 49/0463; H01J 49/40; H01J 49/165; H01J 49/0031; H01J 49/145; H01J 49/0418; H01J 49/164; H01J 49/0404; H01J 49/0445; G01N 33/4833; G01N 33/49; G01N 2030/0085; G01N 2001/045; B23K 26/127; B23K 26/0006; B23K 26/16
USPC ........................................................ 250/288
See application file for complete search history.

(56) References Cited

U.S. PATENT DOCUMENTS 9,202,678 B2 * 12/2015 Dantus ................ H01J 49/162
2015/0301058 A1 * 10/2015 Schettini ............ A61K 39/0011
424/193.1

OTHER PUBLICATIONS

Geertsen, Christian, et al. "Comparison between infrared and ultraviolet laser ablation at atmospheric pressure—implications for solid sampling inductively coupled plasma spectrometry." Journal of analytical atomic spectrometry 9.1 (1994): 17-22.
(Continued)

*Primary Examiner* — Kiet T Nguyen
(74) *Attorney, Agent, or Firm* — Thomas|Horstemeyer, LLP; Stephanie L. Davy-Jow

(57) ABSTRACT

Laser ablation devices and methods including laser ablation are provided. The ablation devices can include a deep UV laser. Dual-laser ablation devices are also provided. Biomolecules can be ablated using a combination of deep UV laser and nanoelectrospray, resulting in protonated sample molecules.

15 Claims, 15 Drawing Sheets

(51) Int. Cl.

| | |
|---|---|
| G01N 33/483 | (2006.01) |
| G01N 33/49 | (2006.01) |
| B23K 26/12 | (2014.01) |
| H01J 49/16 | (2006.01) |
| B23K 26/00 | (2014.01) |
| B23K 26/16 | (2006.01) |
| H01J 49/00 | (2006.01) |
| G01N 1/04 | (2006.01) |
| G01N 30/00 | (2006.01) |

(52) U.S. Cl.
CPC ........ *H01J 49/40* (2013.01); *G01N 2001/045* (2013.01); *G01N 2030/0085* (2013.01)

(56) References Cited

OTHER PUBLICATIONS

Laskin, Julia, et al. "Tissue imaging using nanospray desorption electrospray ionization mass spectrometry." Analytical chemistry 84.1 (2012): 141-148.
Srinivasan, R. "Ablation of polymers and biological tissue by ultraviolet lasers." Science 234.4776 (1986): 559-565.
Lanekoff, Ingela; et al. "Quantitative mass spectrometry imaging of molecules in biological systems." Advances in chromatography (2017): 43-72.
Amster, I. Jonathan, et al. "Cesium ion desorption ionization with Fourier transform mass spectrometry." Analytical chemistry 59.2 (1987): 313-317.
Eikel, Daniel, et al. "Liquid extraction surface analysis mass spectrometry (LESA-MS) as a novel profiling tool for drug distribution and metabolism analysis: the terfenadine example." Rapid Communications in Mass Spectrometry 25.23 (2011): 3587-3596.
Schiebel, Hans Martin; et al. "Soft ionization of biomolecules: A comparison of ten ionization methods for corrins and vitamin B12." Mass Spectrometry Reviews 5.3 (1986): 249-311.
Otsuka, Yoichi, et al. "Imaging mass spectrometry of a mouse brain by tapping-mode scanning probe electrospray ionization " Analyst 139.10 (2014): 2336-2341.
Kinsel, Gary R; et al. "Fragmentation of vitamin B12 during 337 nm matrix-assisted laser desorption ionization." Biological mass spectrometry 23.4 (1994): 205-211.
Laskin, Julia; et al. "Ambient mass spectrometry imaging using direct liquid extraction techniques." Analytical chemistry 88.1 (2016): 52-73.
He, Lin; et al. "Fragmentation of vitamin B 12 in aerosol matrix-assisted laser desorption ionization." Journal of the American Society for Mass Spectrometry 8.2 (1997): 140-147.
Prideaux, Brendan, et al. "Mass spectrometry imaging of levofloxacin distribution in TB-infected pulmonary lesions by MALDI-MSI and continuous liquid microjunction surface sampling." International journal of mass spectrometry 377 (2015): 699-708.
Nemes, Peter; et al. "Internal energy deposition and ion fragmentation in atmospheric-pressure mid-infrared laser ablation electrospray ionization." Physical Chemistry Chemical Physics 14.7 (2012): 2501-2507.
Rao, Wei; et al. "High resolution tissue imaging using the single-probe mass spectrometry under ambient conditions." Journal of The American Society for Mass Spectrometry 26.6 (2015): 986-993.
Barber, Michael, et al. "Fast atom bombardment mass spectrometry of cobalamines." Biomedical Mass Spectrometry 8.10 (1981): 492-495.
Monge, Maria Eugenia, et al. "Mass spectrometry: recent advances in direct open air surface sampling/ionization." Chemical reviews 113.4 (2013): 2269-2308.
Blankenship, J. F; et al. "Matrix effects on the fragmentation of vitamin B12 in plasma desorption mass spectrometry ." Rapid communications in mass spectrometry 11.1 (1997): 143-147.
Goloviev, V. V., et al. "Laser-induced acoustic desorption." International journal of mass spectrometry and ion processes 169 (1997): 69-78.
Guenther, Sabine, et al. "AP-MALDI imaging of neuropeptides in mouse pituitary gland with 5μm spatial resolution and high mass accuracy." International Journal of Mass Spectrometry 305 2-3 (2011): 228-237.
Cheng, Sy-Chyi, et al. "Using laser-induced acoustic desorption/electrospray ionization mass spectrometry to characterize small organic and large biological compounds in the solid state and in solution under ambient conditions." Analytical chemistry 81 3 (2009): 868-874.
Fahy, Eoin, et al. "LIPID MAPS online tools for lipid research." Nucleic acids research 35.suppl_2 (2007): W606-W612.
Hankin, Joseph A; et al. "Sublimation as a method of matrix application for mass spectrometric imaging." Journal of the American Society for Mass Spectrometry 18.9 (2007): 1646-1652.
Jackson, Shelley N; et al. "In situ structural characterization of phosphatidylcholines in brain tissue using MALDI-MS/MS." Journal of the American Society for Mass Spectrometry 16.12 (2005): 2052-2056.
Russo, Richard E., et al. "Laser ablation in analytical chemistry—a review." Taianta 57.3 (2002): 425-451.
Yablon, Andrew D., et al. "Measurement of tissue absorption coefficients by use of interferometric photothermal spectroscopy " Applied optics 38.7 (1999): 1259-1272.
Fisher, Brian T; et al. "Measurement of small-signal absorption coefficient and absorption cross section of collagen for 193-nm excimer laser light and the role of collagen in tissue ablation." Applied optics 43.29 (2004): 5443-5451.
Dodero, Veronica Isabel; et al. "Biomolecular studies by circular dichroism." (2011).
Nazari, Milad; et al. "Polarity switching mass spectrometry imaging of healthy and cancerous hen ovarian tissue sections by infrared matrix-assisted laser desorption electrospray ionization (IR-MALDESI)." Analyst 141.2 (2016) 595-605.
Lembares, Annamarie; et al. "Absorption spectra of corneas in the far ultraviolet region." Investigative ophthalmology & visual science 38.6 (1997): 1283-1287.
Klein, Dustin R; et al. "Structural characterization of phosphatidylcholines using 193 nm ultraviolet photodissociation mass spectrometry." Analytical chemistry 89.3 (2017): 1516-1522.
Little, Mark W; et al. "Wavelength dependence of soft infrared laser desorption and ionization." The Journal of Physical Chemistry C 111.3 (2007): 1412-1416.
Staveteig, Paul T; et al. "Dynamic 193-nm optical properties of water." Applied optics 35.19 (1996): 3392-3403.
Cramer, Rainer; et al. "Matrix-assisted laser desorption and ionization in the O—H and C=O absorption bands of aliphatic and aromatic matrices: dependence on laser wavelength and temporal beam profile." International journal of mass spectrometry and ion processes 169 (1997): 51-67.
Spengler, B., et al. "Excimer laser desorption mass spectrometry of biomolecules at 248 and 193 nm." Journal of Physical Chemistry 91 26 (1987): 6502-6506.
Sheffer, Jay D; et al. "Infrared matrix-assisted laser desorption/ionization using OH, NH and CH vibrational absorption." Rapid communications in mass spectrometry 12.22 (1998): 1685-1690.
Brodbelt, Jennifers. "Photodissociation mass spectrometry: new tools for characterization of biological molecules." Chemical Society Reviews 43.8 (2014): 2757-2783.
Menzel, Christoph, et al. "Mechanisms of energy deposition in infrared matrix-assisted laser desorption/ionization mass spectrometry." International Journal of Mass Spectrometry 207.1-2 (2001): 73-96.
Zhigilei, Leonid V; et al. "Microscopic mechanisms of laser ablation of organic solids in the thermal and stress confinement irradiation regimes." Journal of Applied Physics 88 3 (2000): 1281-1298.
Aesa, A. A; et al. "193 nm ArF laser ablation and patterning of chitosan thin films." Applied Physics A 124.6 (2018) 1-10.
Parrish, John A. "Ultraviolet-laser ablation." Archives of dermatology 121.5 (1985): 599-600.

(56) References Cited

OTHER PUBLICATIONS

Musapelo, Thabiso; et al. "Particle formation in ambient MALDI plumes." Analytical chemistry 83.17 (2011): 6601-6608.

Huang, Min-Zong, et al. "Direct protein detection from biological media through electrospray-assisted laser desorption ionization/mass spectrometry." Journal of proteome research 5.5 (2006): 1107-1116.

Cao, Fan; et al. "Particle size measurement from infrared laser ablation of tissue." Analyst 141.1 (2016): 183-190.

Srinivasan, R; et al. "Ultraviolet laser ablation of organic polymers." Chemical Reviews 89.6 (1989): 1303-1316.

Apitz, I; et al. "Material ejection in nanosecond Er: YAG laser ablation of water, liver, and skin." Applied Physics A 81.2 (2005): 329-338.

Srinivasan, R; et al. "Ablative photodecomposition: action of far-ultraviolet (193 nm) laser radiation on poly (ethylene terephthalate) films." Journal of the American chemical Society 104.24 (1982): 6784-6785.

Linsker, Ralph, et al. "Far-ultraviolet laser ablation of atherosclerotic lesions." Lasers in surgery and medicine 4.2 (1984): 201-206.

Srinivasan, R. "Dynamics of the ultraviolet laser ablation of corneal tissue." AIP Conference Proceedings. Vol. 160. No. 1. American Institute of Physics, 1987.

Davis, G. M., et al. "Spectroscopic studies of ArF laser photoablation of PMMA." Applied Physics A 36.1 (1985): 27-30.

Chen, Huanwen, et al. "Neutral desorption sampling of living objects for rapid analysis by extractive electrospray onization mass spectrometry." Angewandte Chemie 119 40 (2007): 7735-7738.

Cooks, R. Graham, et al. "Ambient mass spectrometry." Science 311.5767 (2006): 1566-1570.

Bodzon-Kulakowska; et al. "Imaging mass spectrometry: instrumentation, applications, and combination with other visualization techniques." Mass spectrometry reviews 35.1 (2016): 147-169.

Huang, Min-Zong, et al. "Ambient ionization mass spectrometry." Annual review of analytical chemistry 3 (2010) 43-65.

Wu, Chunping, et al. "Mass spectrometry imaging under ambient conditions." Mass spectrometry reviews 32.3 (2013) 218-243.

Ovchinnikova, Olga S; et al. "Combining laser ablation/liquid phase collection surface sampling and high-performance iquid chromatography—electrospray ionization-mass spectrometry." Analytical chemistry 83.6 (2011): 1874-1878.

Hsu, Cheng-Chih; et al. "Visualizing life with ambient mass spectrometry." Current Opinion in Biotechnology 31 (2015) 24-34.

Huang, Min-Zong, et al. "Effects of matrix, electrospray solution, and laser light on the desorption and ionization mechanisms in electrospray-assisted laser desorption ionization mass spectrometry" Analyst 135.4 (2010): 759-766.

Takats, Zoltan, et al. "Mass spectrometry sampling under ambient conditions with desorption electrospray ionization." Science 306. 5695 (2004): 471-473.

Cody, Robert B; et al. "Versatile new ion source for the analysis of materials in open air under ambient conditions." Analytical chemistry 77.8 (2005): 2297-2302.

Laiko, Victor V; et al. "Atmospheric pressure matrix-assisted laser desorption/ionization mass spectrometry." Analytical Chemistry 72.4 (2000): 652-657.

Laiko, Victor V., et al. "Desorption/ionization of biomolecules from aqueous solutions at atmospheric pressure using an infrared laser at 3 μm." Journal of the American Society for Mass Spectrometry 13.4 (2002): 354-361.

Li, Yue; et al. "Atmospheric pressure molecular imaging by infrared MALDI mass spectrometry." Analytical Chemistry 79.2 (2007): 523-532.

Coello, Yves, et al. "Atmospheric pressure femtosecond laser imaging mass spectrometry." Analytical chemistry 82.7 (2010): 2753-2758.

Gray, Alan L. "Solid sample introduction by laser ablation for inductively coupled plasma source mass spectrometry." Analyst 110.5 (1985): 551-556.

Russo, Richard E., et al. "Femtosecond laser ablation ICP-MS." Journal of Analytical Atomic Spectrometry 17.9 (2002) 1072-1075.

Russo, Richard E., et al. "Laser ablation in analytical chemistry." (2013): 6162-6177.

Coon, Joshua J; et al. "Atmospheric pressure laser desorption/chemical ionization mass spectrometry: a new ionization method based on existing themes." Rapid communications in mass spectrometry 16.7 (2002): 681-685.

Peng, Wen-Ping, et al. "Laser-induced acoustic desorption mass spectrometry of single bioparticles." Angewandte Chemie International Edition 45.9 (2006): 1423-1426.

Nyadong, Leonard, et al. "Atmospheric pressure laser-induced acoustic desorption chemical ionization mass spectrometry for analysis of saturated hydrocarbons" Analytical chemistry 84.16 (2012): 7131-7137.

Roach, Patrick J; et al. "Nanospray desorption electrospray ionization: an ambient method for liquid-extraction surface sampling in mass spectrometry" Analyst 135.9 (2010): 2233-2236.

Vaikkinen, Anu, et al. "Infrared laser ablation atmospheric pressure photoionization mass spectrometry." Analytical chemistry 84.3 (2012): 1630-1636.

Weston, Daniel J. "Ambient ionization mass spectrometry: current understanding of mechanistic theory; analytical performance and application areas." Analyst 135.4 (2010): 661-668.

Nemes, Peter; et al. "Simultaneous imaging of small metabolites and lipids in rat brain tissues at atmospheric pressure by laser ablation electrospray ionization mass spectrometry" Analytical chemistry 82.3 (2010): 982-988.

Weston, Daniel J., et al. "Direct analysis of pharmaceutical drug formulations using ion mobility spectrometry/quadrupole-time-of-flight mass spectrometry combined with desorption electrospray ionization." Analytical chemistry 77.23 (2005): 7572-7580.

Shiea, Jentaie, et al. "Electrospray-assisted laser desorption/ionization mass spectrometry for direct ambient analysis of solids." Rapid Communications in Mass Spectrometry: An International Journal Devoted to the Rapid Dissemination of Up-to-the-Minute Research in Mass Spectrometry 19.24 (2005): 3701-3704.

Williams, Jonathan P., et al. "The use of recently described ionisation techniques for the rapid analysis of some common drugs and samples of biological origin." Rapid Communications in Mass Spectrometry: An International Journal Devoted to the Rapid Dissemination of Up-to-the-Minute Research in Mass Spectrometry 20.9 (2006) 1447-1456.

Sampson, Jason S; et al. "Generation and detection of multiply-charged peptides and proteins by matrix-assisted laser desorption electrospray ionization (MALDESI) Fourier transform ion cyclotron resonance mass spectrometry." Journal of the American Society for Mass Spectrometry 17.12 (2006): 1712-1716.

Fernandez, Facundo M., et al. "Characterization of solid counterfeit drug samples by desorption electrospray ionization and direct-analysis-in-real-time coupled to time-of-flight mass spectrometry." ChemMedChem: Chemistry Enabling Drug Discovery 1.7 (2006): 702-705.

Brady, John J; et al. "Mass spectrometry of intact neutral macromolecules using intense non-resonant femtosecond laser vaporization with electrospray post-ionization." Rapid Communications in Mass Spectrometry: An International Journal Devoted to the Rapid Dissemination of Up-to-the-Minute Research in Mass Spectrometry 23.19 (2009) 3151-3157.

Pan, Zhengzheng, et al. "Principal component analysis of urine metabolites detected by NMR and DESI-MS in patients with inborn errors of metabolism." Analytical and bioanalytical chemistry 387.2 (2007): 539-549.

Nemes, Peter; et al. "Laser ablation electrospray ionization for atmospheric pressure, in vivo, and imaging mass spectrometry." Analytical chemistry 79.21 (2007): 8098-8106.

Jackson, Ayanna U., et al. "Direct analysis of Stevia leaves for diterpene glycosides by desorption electrospray ionization mass spectrometry." Analyst 134.5 (2009): 867-874.

Rezenom, Yohannes H; et al. "Infrared laser-assisted desorption electrospray ionization mass spectrometry." Analyst 133.2 (2008): 226-232.

(56) References Cited

OTHER PUBLICATIONS

Morlock, Gertrud; et al. "Determination of isopropylthioxanthone (ITX) in milk, yoghurt and fat by HPTLC-FLD, HPTLC-ESI/MS and HPTLC-DART/MS." Analytical and bioanalytical chemistry 385.3 (2006): 586-595.
Sampson, Jason S; et al. "Intact and top-down characterization of biomolecules and direct analysis using infrared matrix-assisted laser desorption electrospray ionization coupled to FT-ICR mass spectrometry." Journal of the American Society for Mass Spectrometry 20.4 (2009): 667-673.
Vaclavik, Lukas, et al. "Ambient mass spectrometry employing direct analysis in real time (DART) ion source for olive oil quality and authenticity assessment." Analytica Chimica Acta 645.1-2 (2009): 56-63.
Galhena, Asiri S., et al. "Small molecule ambient mass spectrometry imaging by infrared laser ablation metastable-induced chemical ionization " Analytical chemistry 82.6 (2010): 2178-2181.
Xu, Jiaquan, et al. "Quantitative determination of bulk molecular concentrations of ß-agonists in pork tissue samples by direct internal extractive electrospray ionization-mass spectrometry" Analytical chemistry 89.21 (2017): 11252-11258.
Judge, Elizabeth J., et al. "Nonresonant femtosecond laser vaporization with electrospray postionization for ex vivo plant tissue typing using compressive linear classification." Analytical chemistry 83.6 (2011): 2145-2151.
Campbell, Dahlia L, et al. "Improved spatial resolution in the imaging of biological tissue using desorption electrospray ionization " Analytical and bioanalytical chemistry 404.2 (2012): 389-398.
Zou, Jing, et al. "Ambient mass spectrometry imaging with picosecond infrared laser ablation electrospray ionization (PIR-LAESI)." Analytical chemistry 87 24 (2015): 12071-12079.
Wiseman, Justin M., et al. "Tissue imaging at atmospheric pressure using desorption electrospray ionization (DESI) mass spectrometry." Angewandte Chemie International Edition 45.43 (2006): 7188-7192.
Fowble, Kristen L., et al. "Development of "laser ablation direct analysis in real time imaging" mass spectrometry: Application to spatial distribution mapping of metabolites along the biosynthetic cascade leading to synthesis of Atropine and scopolamine in plant tissue." Analytical chemistry 89.6 (2017): 3421-3429.
Wiseman, Justin M., et al. "Desorption electrospray ionization mass spectrometry: Imaging drugs and metabolites in tissues." Proceedings of the National Academy of Sciences 105.47 (2008): 18120-18125.
Kuznetsov, Ilya, et al. "Three-dimensional nanoscale molecular imaging by extreme ultraviolet laser ablation mass spectrometry." Nature communications 6.1 (2015): 1-6.
Calligaris, David, et al. "Application of desorption electrospray ionization mass spectrometry imaging in breast cancer margin analysis." Proceedings of the National Academy of Sciences 111.42 (2014): 15184-15189.
Nang, Hao AO, et al. "Fast chemical imaging at high spatial resolution by laser ablation inductively coupled plasma mass spectrometry." Analytical chemistry 85.21 (2013): 10107-10116.
Gerbig, Stefanie, et al. "Analysis of colorectal adenocarcinoma tissue by desorption electrospray ionization mass spectrometric imaging." Analytical and bioanalytical chemistry 403.8 (2012): 2315-2325.
Giesen, Charlotte, et al. "Highly multiplexed imaging of tumor tissues with subcellular resolution by mass cytometry." Mature methods 11.4 (2014): 417-422.
Eberlin, Livia S., et al. "Classifying human brain tumors by lipid imaging with mass spectrometry." Cancer research 72.3 (2012): 645-654.
Gorodetsky, G., et al. "Calorimetric and acoustic study of ultraviolet laser ablation of polymers." Applied physics letters 46.9 (1985): 828-830.
Kitai, Moishe S., et al. "The physics of UV laser cornea ablation." IEEE journal of quantum electronics 27.2 (1991) 302-307.
Vogel, Alfred; et al. "Mechanisms of pulsed laser ablation of biological tissues." Chemical reviews 103.2 (2003) 577-644.

\* cited by examiner

DEVICES AND METHODS FOR DEEP UV LASER ABLATION

CROSS-REFERENCE TO RELATED APPLICATIONS

This application claims the benefit of and priority to U.S. Provisional Application Ser. No. 62/856,710, having the title "DEVICES AND METHODS FOR DEEP UV LASER ABLATION", filed on Jun. 3, 2019, the disclosure of which is incorporated herein by reference in its entirety.

STATEMENT REGARDING FEDERALLY SPONSORED RESEARCH OR DEVELOPMENT

This invention was made with government support under contract R21 EB023110 awarded by the National Institutes of Health. The government has certain rights in the invention.

TECHNICAL FIELD

The present disclosure generally relates to mass spectrometry.

BACKGROUND

Current approaches to microdissection tissue sampling either use an infrared laser or near-ultraviolet and require time- and labor-intensive extraction processes for high-precision chemical analyses of tissue samples at or below the single cell level. There remains a need for devices and methods that overcome the aforementioned deficiencies.

SUMMARY

Embodiments of the present disclosure provide for laser ablation apparatus, Dual-laser ablation apparatus, methods for laser ablation of biomolecules, and the like.

An embodiment of the present disclosure includes an ablation device that includes a deep UV laser, an electrospray ion source having an electrospray emitter and a sample target coupled to a mass spectrometer.

An embodiment of the present disclosure also includes a dual-laser ablation device, having a first laser and a second laser with adjustable firing time delay, a first focusing lens and a second focusing lens, and an electrospray ion source having an electrospray emitter.

An embodiment of the present disclosure also includes a method for laser ablation of biomolecules. The method includes applying a sample to a target, directing a beam of at least one deep UV laser at the sample, and directing an electrospray at the laser beam. Directing the electrospray at the laser beam results in protonated sample molecules.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 4B) myoglobin; and (FIG. 4C) bovine serum albumin obtained with 193-nm DUV-LA ESI in accordance with embodiments of the present disclosure.

FIG. 8B, myoglobin after ESI only; FIG. 8C, tissue; FIG. 8D, albumin) after DUV-LAESI. DUV LAESI signal last <1 second after laser irradiation.

FIG. 9B, whole blood after IR/UV LAESI; FIG. 9C, tissue after IR LAESI; FIG. 9D, tissue after IR/UV LAESI). Peaks labelled in purple belongs to a protein with MW 15198.8±0.5 Da.

DETAILED DESCRIPTION

Figure 1:
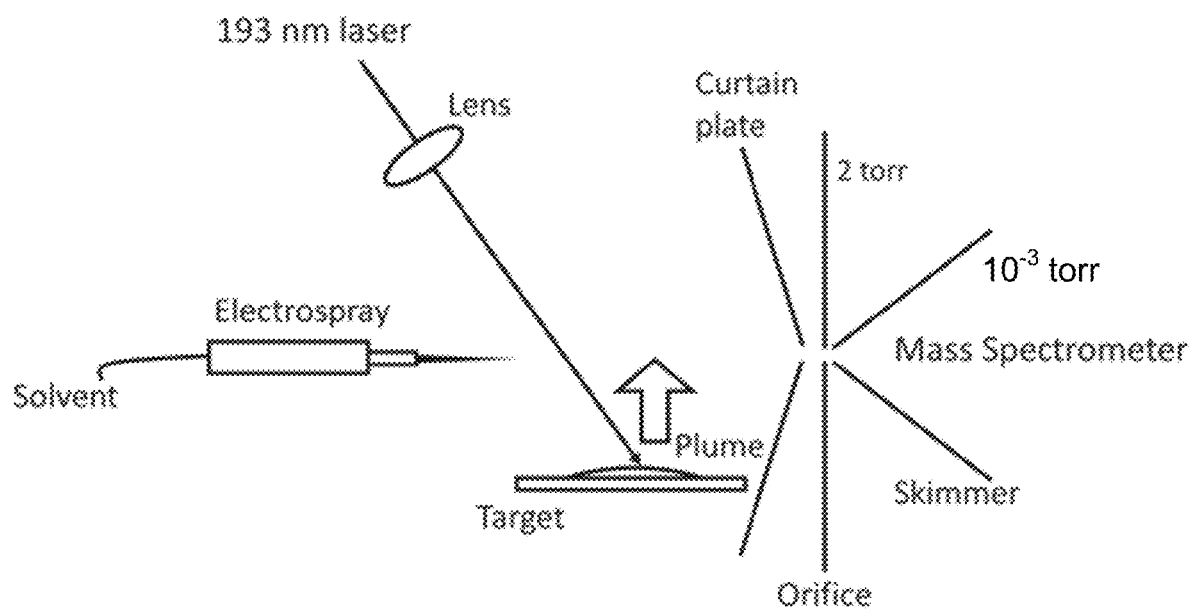
FIG. 1 is a schematic of an embodiment of the DUV-LA ESI source.

In accordance with the purpose(s) of the present disclosure, as embodied and broadly described herein, embodiments of the present disclosure, in some aspects, relate to deep ultraviolet laser ablation (DUV-LA) tissue microdissection instruments, methods of using DUV-LA instruments, methods of microdissection tissue sampling, and the like.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of chemistry, mass spectrometry, and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

In some instances, units may be used herein that are non-metric or non-SI units. Such units may be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 $kN/m^3$; or a unit disclosed 100° F. is intended to mean an equivalent dimension of 37.8° C.; and the like) as understood by a person of ordinary skill in the art.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

GENERAL DISCUSSION

In accordance with the purpose(s) of the present disclosure, as embodied and broadly described herein, embodiments of the present disclosure, in some aspects, relate to devices and methods for laser ablation (also referred to as microdissection).

In general, embodiments of the present disclosure provide for devices for laser ablation and methods of ablating samples.

The present disclosure includes an ablation device including a deep UV laser and electrospray. Advantageously, the combined use of the deep UV laser and the electrospray allows for the detection of protonated analyte molecules, including biomolecules and peptides, without detectable fragmentation. The devices and methods described herein can be used for sample capture for use in mass spectrometry or further analyses such as protein and/or DNA sequencing.

Embodiments of the present disclosure include an ablation as above, wherein the deep UV laser is a pulsed nanosecond 193 nm laser.

Deep wavelength UV laser (also referred to as a short wavelength), as used herein, describes lasers having a wavelength of about 300 to 100 nm, or about 193 nm. Such lasers can include nanosecond excimer lasers, overtones of Nd:YAG lasers, and the like.

Figure 8A:
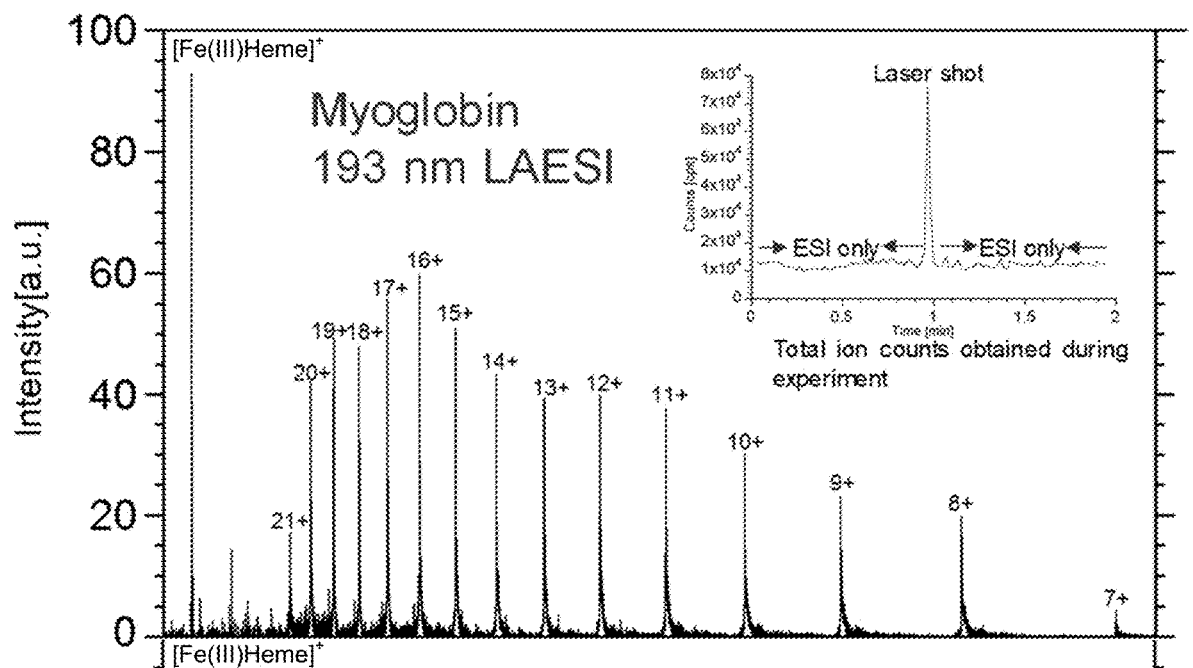
FIGS. 8A-D are mass spectra of protein standards and tissue (FIG. 8A, myoglobin.
Figure 8B:
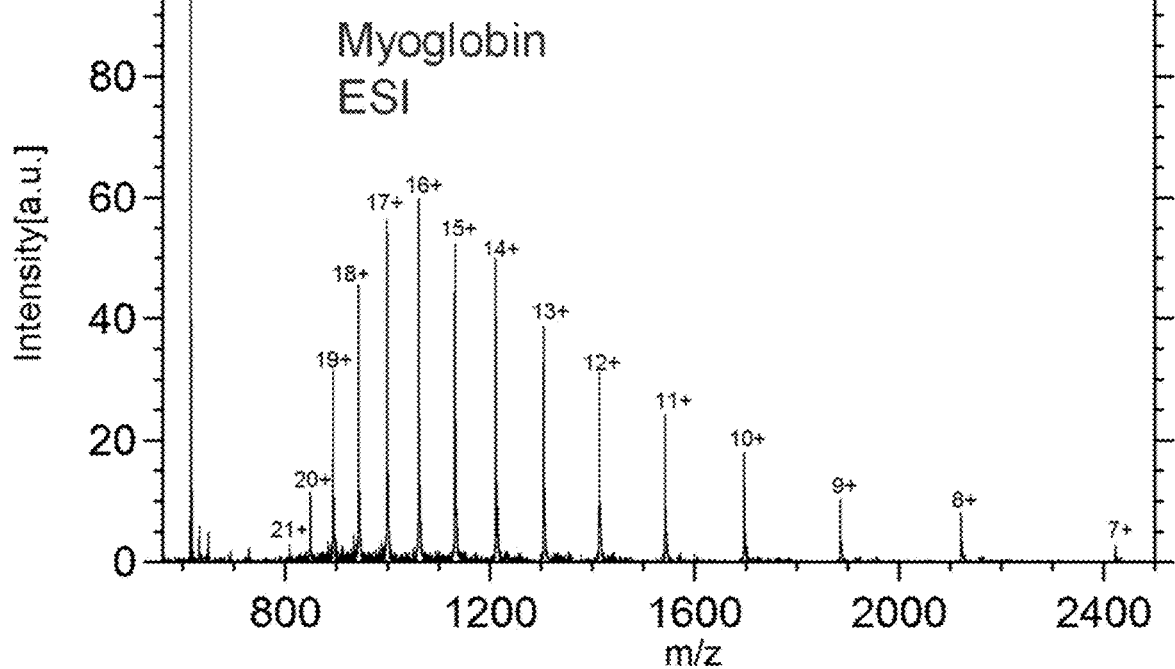
Figure 8C:
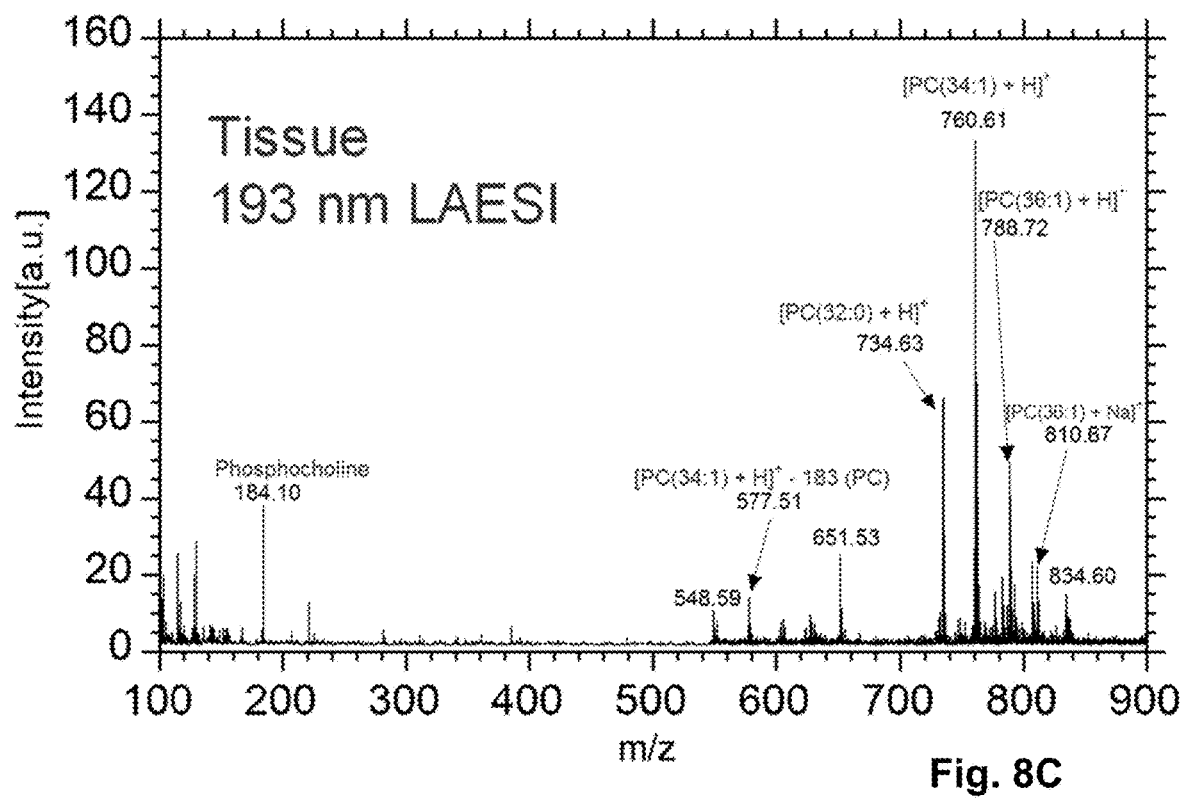
Figure 8D:
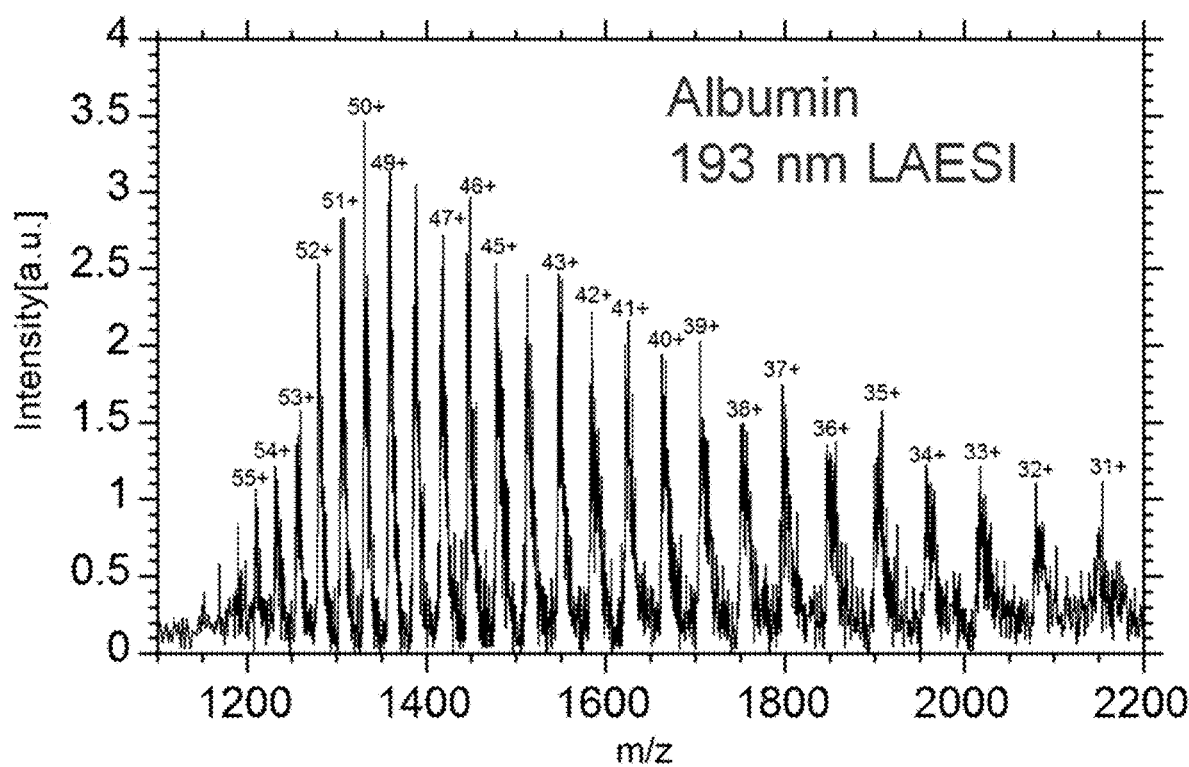

Deep ultra-violet laser ablation (DUV-LA) microdissection instruments and methods have a competitive advantage over all current methods for biomolecule isolation for protein and DNA sequencing. First, DUV-LA has the unique capability to sample on a micrometer size scale and second, it has the ability to sample in conjunction with imaging for localized analysis. Third, this technology is faster because no extraction is required. FIGS. 1 and 8A-8B show embodiments of DUV-LA microdissection. The DUV-LA technology described herein is faster, more accurate, and higher resolution (Table 1) when compared to infrared and near-UV laser capture microdissection (LCM).

The DUV-LA technology of the present disclosure provides an advantage over infrared microdissection because the 193 nm laser wavelength can be focused to a spot size four times smaller than a 810 nm near-infrared laser and does not require additional extraction from the melted plastic of the capture device. The DUV-LA technology has the advantage over UV microdissection because it can be focused to a precision level of more than twice that of 350 nm near-UV lasers, does not require additional extraction, and does not damage the component molecules due to the fast ablation compared to the slow cutting collection mode. Other instruments all require extensive extraction and sample work-up. The approach described here is more accurate and faster because it does not require extraction, as do the LCM approaches. The collection system described herein can be a robotic collection system, wherein the laser ablates material sequentially into an array of vials instead of a single vial.

In an embodiment, the device can be coupled to a LAESI (e.g. 2940 nm) or electrospray laser desorption ionization (ELDI) system (e.g. 266 nm, 355 nm, 532 nm and 1064 nm).

In another embodiment, the device can include an optical microscope and a collection and transportation module that will interface with standard sequencing units. In such a configuration, there is no direct interfacing with a mass spectrometer. The material can instead be ablated from a surface down into a collection vessel. The collection vessel can be such as a single tube or a multi-well plate.

In this respect, the laser ablation technology is coupled with a "capture" portion and its scope can go beyond mass spectrometry analysis (e.g. DNA sequencing).

The present disclosure also includes a dual-laser ablation device including both a deep UV laser and an infrared (IR) laser, along with electrospray.

In both protein and DNA sequencing, there is a strong demand for clinical disease biomarkers and new tools for diagnostics. In addition to having a large and fast growing global market, the laser-ablation microdissection instrument targets an area of important societal need. Biomedical molecular diagnostics with precision spatial resolution is important for clinical and research applications because the heterogeneity of tissue results in important differences in gene expression, proteins, and metabolites that are not easily observed in bulk analysis. Better understanding biological processes with precise spatial localization requires new tools and techniques for biology and medicine. The laser ablation microdissection instrument can allow the precise localization of tumor margins and an assessment of their genetic differences within the tissue. It can also enhance the ability to study stem cell development from a molecular standpoint.

The ability to study the spatially resolved biochemistry of the brain has important implications in understanding neurological diseases and their treatment. The methods and instruments described herein will be an essential tool for sampling tissue for biomedical research and clinical applications.

Currently, both proteins and DNA sequencing applications require a preparative tool to extract the molecular material from the tissue. An increasing number of these applications require spatial selectivity on a micrometer level of precision. The DUV-LA microdissection instrument of the present disclosure provides this capability.

There are a wide number of applications for the methods and devices described herein, including but not limited to forensic genetics, agricultural genomics, and clinical diagnostics. The greatest immediate need for spatially resolved protein and DNA sequencing is in cancer diagnosis and treatment. The biochemistry of cancer cells is highly heterogeneous. As cancers progress, they accumulate molecular changes, thus a spatially resolved sequencing may be necessary for a full assessment of cancer progression. A second application area is brain biochemistry. The ability to study genetic mosaicism and the resulting heterogeneity of the biochemistry in the brain has important implications in understanding neurological diseases and their treatment. This has implications in several diseases such as Parkinson's and Alzheimer's. The ability to perform single cell spatially resolved biochemistry is critical to understanding mosaic variants.

TABLE 1

A comparison of the DUV-LA technology of the present disclosure and alternative technologies for laser microdissection. The disclosed DUV-LA technology is faster, more accurate, and higher resolution than competing instruments

| Instrument | Technology | Wavelength | Problems |
| --- | --- | --- | --- |
| DUV-LA | UV Ablation | 193 nm | — |
| Arcturus ® | IR Melting | 810 nm | Precision, ease of use |
| Zeiss ® | UV Cutting | 337 nm | Fragmentation, ease of use |
| Leica ® | UV Cutting | 350 nm | Fragmentation, ease of use |
| MMI | UV Cutting | 355 nm | Fragmentation, ease of use |

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Deep-Ultraviolet Laser Ablation Electrospray Ionization Mass Spectrometry Ambient mass spectrometry involves the formation of ions outside the mass analyzer without sample preparation.[1-4] Ions are formed when ions or charged droplets impinge on the sample or when a pulsed laser is used to ablate material that then interacts with charge carriers to form ions. Charge to surface ionization can be accomplished using an electrospray ion source directed at a solid sample as with the technique known as desorption electrospray ionization (DESI).[5] Alternatively, ions can be formed by metastable chemical ionization as with direct analysis in real time (DART)[6] when reagent ions are directed at a solid sample. Laser ablation ambient mass spectrometry facilitates removal of sample material from small spots that are a fraction of a millimeter in diameter. The laser ablated material can be directly ionized by infrared laser[7-9] and femtosecond laser matrix-free ionization.[10] An alternative approach is laser post-ionization, a two-step process where the ablation of sample material is followed by post ionization by inductively coupled plasma,[11-13] chemical ionization,[14,15] photoionization,[16] or electrospray ionization.[17-20]

A variety of wavelengths and pulse energies have been used for ambient laser ablation mass spectrometry. An approach called electrospray-assisted laser desorption/ionization (ELDI) uses a 337 nm pulsed nanosecond nitrogen laser combined with electrospray post-ionization and was the first laser ambient method to detect intact proteins.[18] The matrix-assisted laser desorption electrospray ionization (MALDESI) technique uses a matrix of the type used in matrix-assisted laser desorption ionization (MALDI) to enhance material removal with UV laser ablation.[19] Infrared lasers can be used to ablate material by absorption of vibrational energy by the sample. An early example is the use of a 10.6 μm $CO_2$ laser to ablate biomolecules for chemical ionization.[14] Mid-IR lasers can be used to excite the OH stretch of water and other compounds containing OH and NH groups. Several configurations have been used to couple nanosecond IR laser ablation with electrospray[21-23] which is most often referred to as laser ablation electrospray ionization (LAESI). Mid-IR lasers have been used with chemical ionization to form a technique known as infrared laser ablation metastable-induced chemical ionization (IR-LAMICI).[24] These mid-IR ablation methods are efficient at ablation of many types of samples using endogenous water as the matrix.

Picosecond and femtosecond lasers have also been used for laser ablation coupled with electrospray ionization. An 800 nm 75 fs pulsed laser was used to ablate material for ionization by electrospray in laser electrospray mass spectrometry (LEMS).[25] The advantage of the fs laser is that it provides efficient ablation without requiring resonant absorption. A 2.88 μm wavelength and 80 ps pulse width a high peak power infrared laser was coupled with electrospray for pulsed infrared laser ablation electrospray ionization (PIR-LAESI).[26]

The use of lasers with wavelengths in the deep ultraviolet region (ca. 200 nm) and beyond for biological mass spectrometry has been reported recently. For example, a Nd:YAG laser fifth harmonic at 213 nm wavelength was used with direct analysis in real time (DART) ionization for ambient mass spectrometry imaging of intact small molecules and metabolites in tissue.[27] Three-dimensional imaging of intact molecules up to 500 m/z has also been demonstrated using a 47 nm soft X-ray laser for both desorption and ionization.[28] A 193 nm excimer laser was used for ablation of tissue treated with heavy-metal tagged antibodies and post ionized with inductively coupled plasma mass spectrometry.[29,30] These short wavelength lasers can be focused to small spot sizes for efficient ablation[31] with minimal thermal damage to adjacent areas of the sample.[32] The short wavelength pulses are absorbed by a broad range of compounds. Despite these advantages,[31] deep UV pulsed laser ablation has been limited in application to atoms and small molecules.

In DUV-LAESI, a pulsed nanosecond 193 nm laser was used to demonstrate laser ablation electrospray ionization mass spectrometry of intact biomolecules. The UV laser would be expected to fragment fragile biomolecules, especially large biomolecules such as proteins. Samples were deposited on a metal target held a few millimeters below the inlet of a hybrid quadrupole time-of-flight mass spectrometer with an electrospray emitter held at the same height as the mass spectrometer inlet. The laser ablates material from the sample that is entrained in the cone of the electrospray tip, which results in highly charged molecules. The system was used to demonstrate the detection of intact peptides and proteins from pure compounds and lipids from tissue samples.

Methods and Materials

The configuration used for deep-ultraviolet laser ablation coupled with electrospray is similar to that reported previously for infrared laser ablation;[22] a diagram of the deep ultraviolet laser ablation electrospray ionization (DUV-LAESI) ion source is shown in FIG. 1. The wavelength of the present disclosure is differs from previous work, based on the change in the type of laser used (gas vs. solid state). A quadrupole time-of-flight mass spectrometer (QSTAR XL, Applied Biosystems, Framingham, Mass.) was used with the nanoelectrospray ion source and custom spray tip. A 193 nm ArF excimer laser (OPTex, Lambda Physik, Fort Lauderdale, Fla.) was used at a repetition rate of 5 Hz. The laser was mounted on an optical breadboard adjacent to the ion source. The laser beam was directed onto the sample target using UV fused silica right-angle prisms and was focused with a 10 mm focal length calcium fluoride lens to a 450×200 μm spot. A 4×1 cm stainless steel sample target was mounted 5 mm below and 4 mm away from the mass spectrometer inlet. The laser incidence angle was 60° from the target surface normal and a laser fluence of 11 kJ/m$^2$ was used for all experiments unless otherwise indicated. The electrospray emitter was made from a 50 μm ID, 360 μm OD fused silica capillary (Polymicro Technologies, Phoenix, Ariz., USA) pulled manually after exposing it to the flame of a butane torch to a ca. 10 μm diameter tip. The tip was placed 8 mm from the mass spectrometer inlet. An equal volume mixture of methanol and water containing 0.1% aqueous trifluoroacetic acid was infused through the capillary at a flow rate of 1 μL/min with a syringe pump (Cole-Parmer, Vernon Hills, Ill., USA). A potential of 5.5 kV was applied to the emitter.

Human angiotensin II, bradykinin acetate salt, bovine insulin, cytochrome c from equine heart, hemoglobin, ubiquitin, myoglobin, bovine serum albumin (BSA) and LC-MS grade water were purchased from Sigma-Aldrich (St Louis, Mo., USA). Trifluoroacetic acid (99.5%, LC-MS grade) was obtained from Thermo Fisher Scientific (Waltham, Mass., USA) and methanol (LC-MS grade) was purchased from EMD Millipore (Burlington, Mass., USA). Baseline correction and data point reduction of acquired mass spectra were achieved using a LabVIEW routine. The B-spline algorithm was used to calculate the spectrum baseline while data reduction was achieved by averaging.

Analytes were dissolved in water to a concentration of 1 mg/ml and insulin solutions contained 0.1% TFA to facilitate dissolution. The samples were vortexed until complete dissolution. A 10 μL aliquot of each sample was deposited onto the target by pipette and vacuum dried. For conventional ESI analysis, each solution was further diluted with 1:1 methanol/water 0.1% TFA solution to achieve the desired concentration.

Brain tissue was collected from 6 weeks old rats using procedures approved by the LSU Institutional Animal Care and Use Committee (IACUC) at the LSU School of Veterinary Medicine, Division of Laboratory Animal Medicine (DLAM). The animals were sacrificed via carbon dioxide exposure (5 psi) according to the American Veterinary Medical Association (AVMA) guidelines for the euthanasia of animals. The tissue was removed and immediately frozen with liquid nitrogen. 50 μm thick tissue sections were thaw-mounted on a microscope slide at −20° C. using a cryostat (CM 1850, Leica Microsystems, Wetzlar, Germany) and stored at −80° C. prior to use. Mounted tissue sections were thawed and vacuum dried for 10 min prior to sampling.

Results and Discussion

Figure 2A:
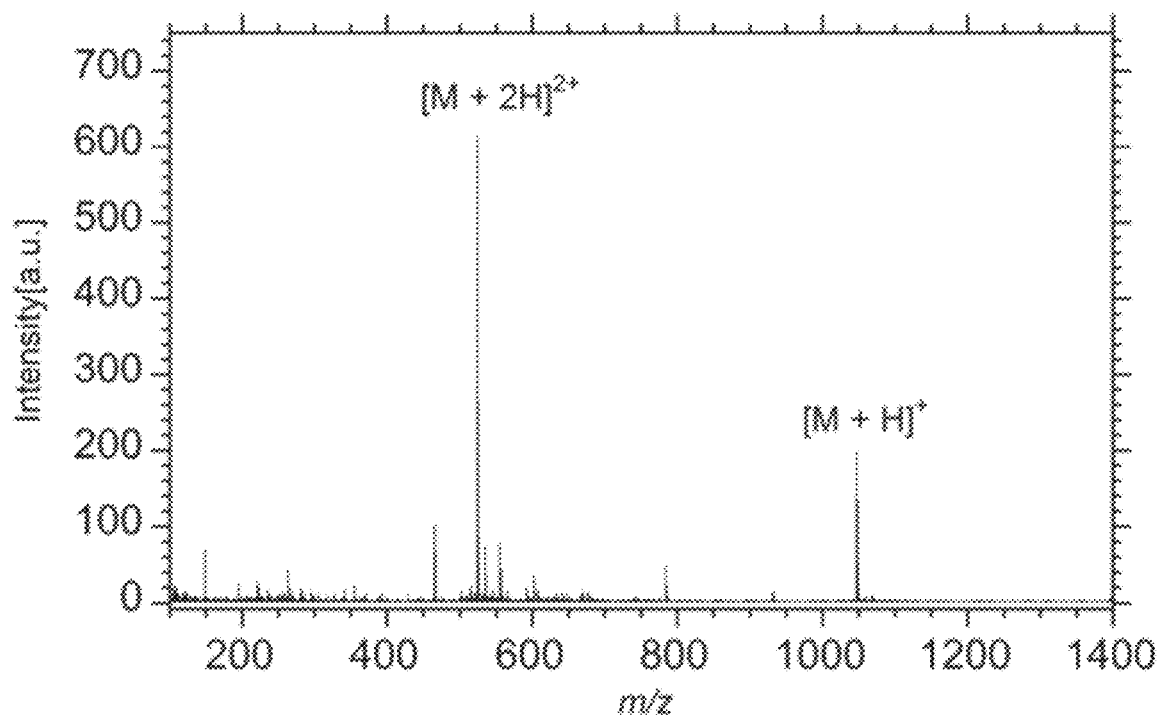
FIGS. 2A and 2B provide mass spectra of angiotensin II acquired with (FIG. 2A) 193-nm DUV-LA ESI and (FIG. 2B) conventional ESI using a 50-μM angiotensin II solution, in accordance with embodiments of the present disclosure.
Figure 2B:
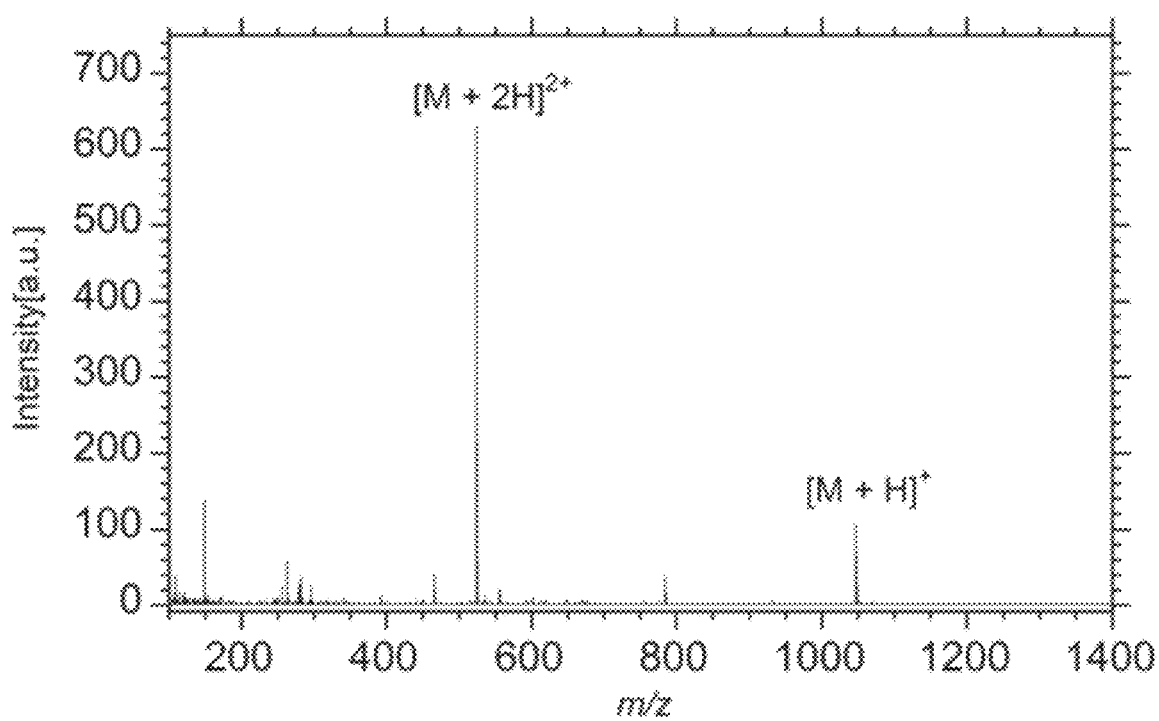
Figure 10A:
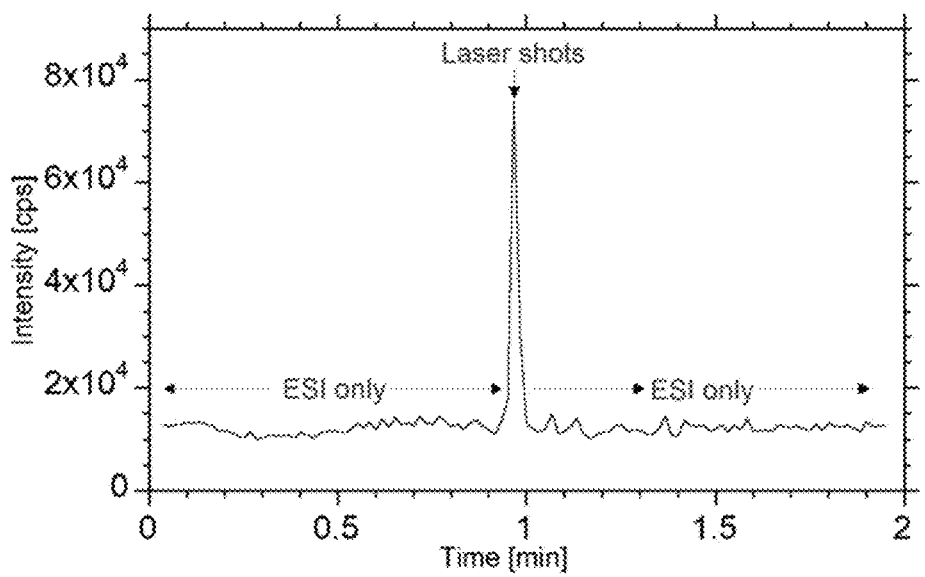
FIG. 10A shows the total ion current (TIC) acquired during DUV-LAESI showing the ion signal with electrospray alone and the ion signal with both electrospray and laser; the analyte signal lasted for ~3 seconds.
Figure 10B:
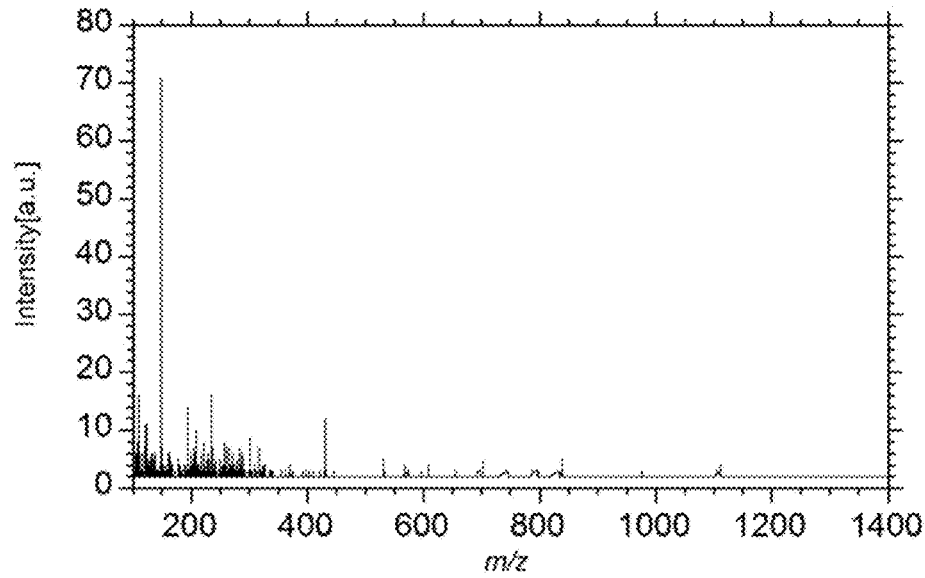
FIG. 10B is an example of DUV-LAESI experiment with electrospray only and FIG. 10C with laser only.
Figure 10C:
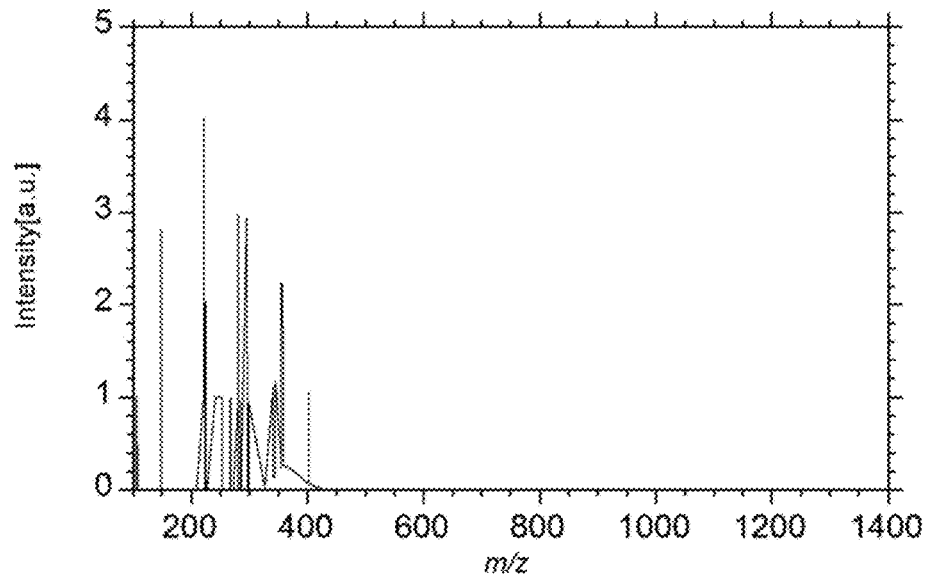
Figure 11A:
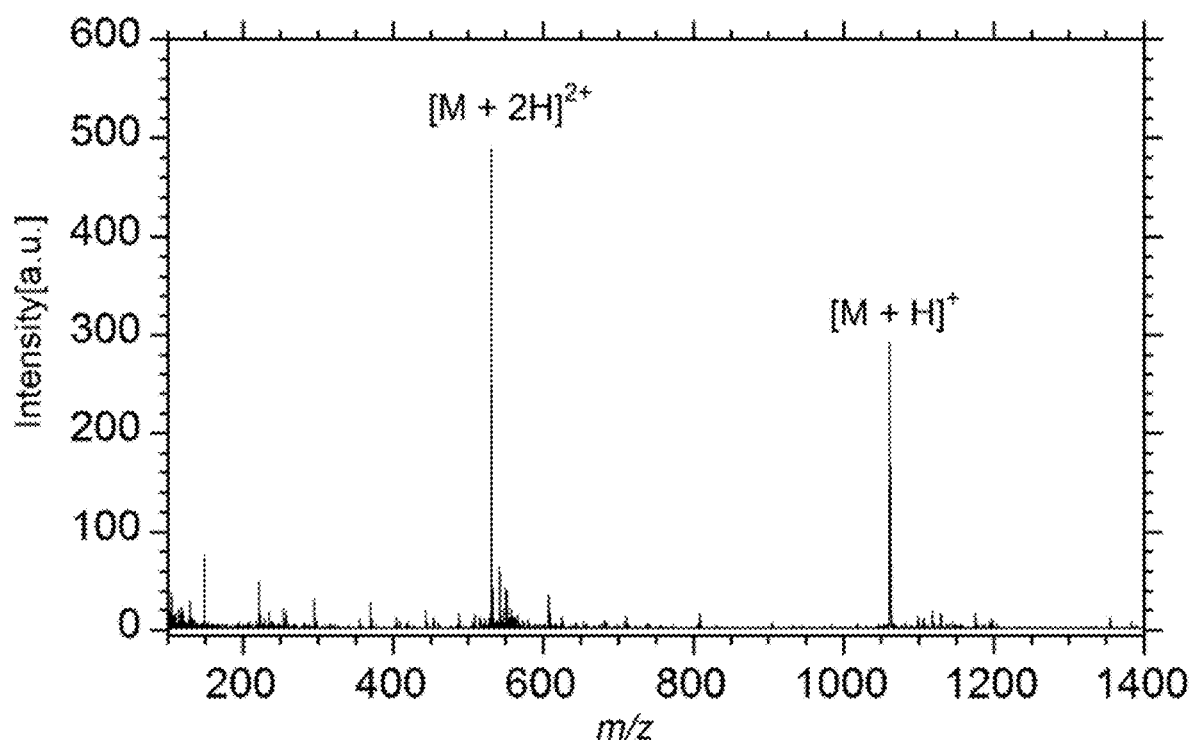
FIGS. 11A-11B provide single acquisition mass spectra of bradykinin using DUV-LAESI (FIG. 11A) and ESI of 50 μM solution (FIG. 11B). Sodium and potassium adducts adjacent to the doubly charged peak as well as low intensity orifice-skimmer induced fragments are observed in both spectra.
Figure 11B:
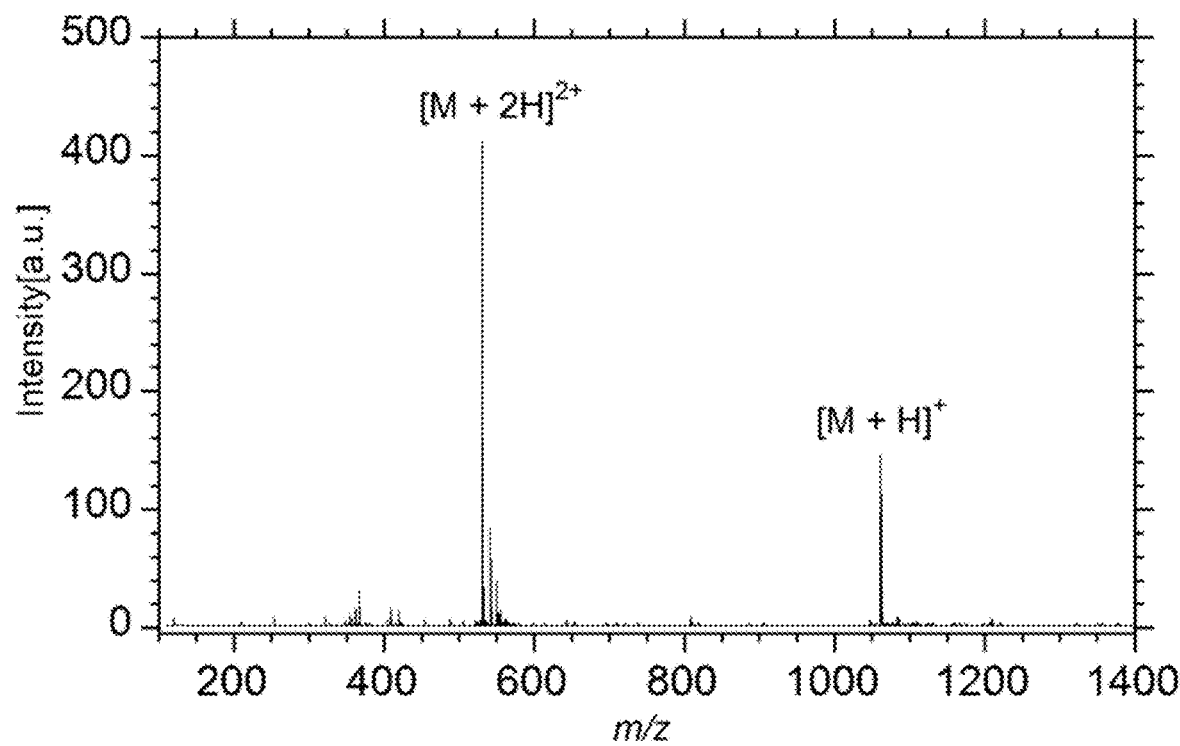

Initial experiments were conducted using peptide standards. Angiotensin II dried droplet samples were ablated at 193 nm and the plume was intercepted by the ESI spray producing spectra with singly and doubly charged ions. The entirety of the sample in the irradiated spot was completely ablated after about 20 laser shots. Mass spectra of angiotensin obtained by UV laser ablation electrospray and conventional electrospray are shown in FIGS. 2A-2B. The mass spectrum in FIG. 2A results from a single acquisition mass spectrum of 193 nm ablation of angiotensin II after ca. 5 seconds of laser irradiation. The analyte signal lasted for 3 seconds after the onset of the laser ablation as shown in the total ion signal recorded during the experiment (FIGS. 10A-10C). A conventional electrospray mass spectrum of angiotensin from infusion of a 50 μM angiotensin II solution is shown in FIG. 2B. The spectra are similar except for larger $Na^+$ and $K^+$ peaks in the DUV-LAESI mass spectrum. Some nozzle-skimmer fragmentation denoted with asterisks is observed in both spectra. Sample mass spectra could only be obtained with the combination of electrospray and laser. When the laser was operated without the electrospray or the electrospray without the laser, no peaks corresponding to protonated analyte molecules were detected (FIGS. 10A-10C). Experiments using bradykinin peptide were also performed (FIGS. 11A-11B) and confirmed the results obtained with angiotensin II.

Figure 3A:
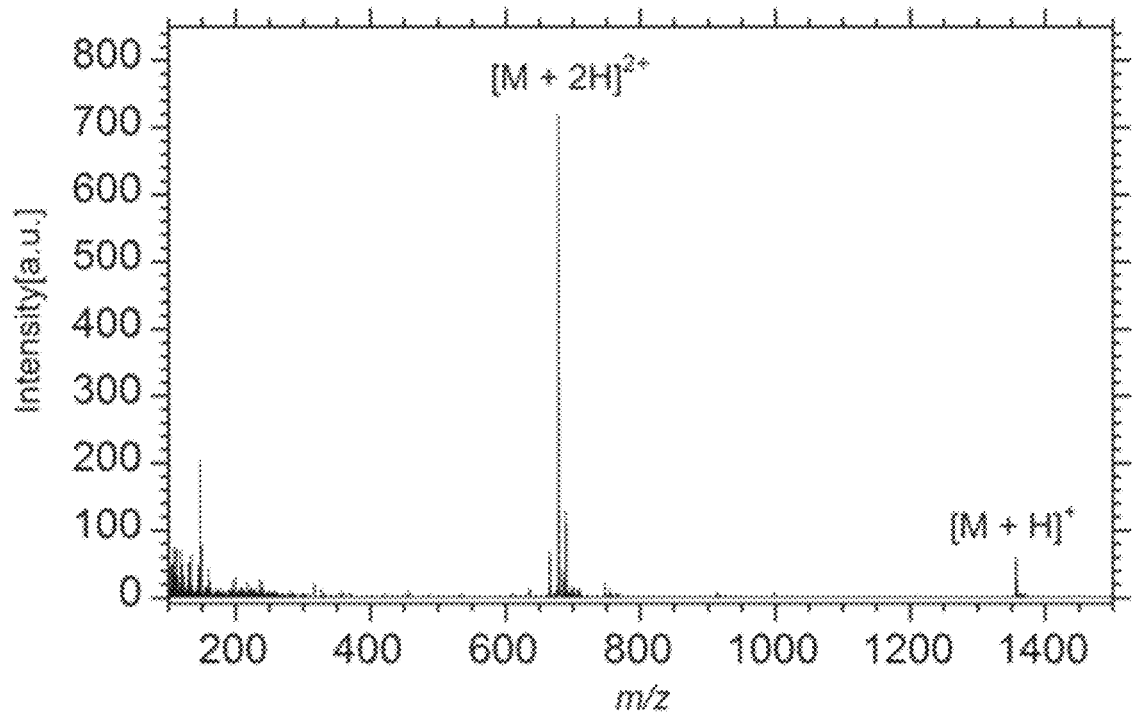
FIGS. 3A and 3B provide mass spectra of vitamin $B_{12}$ acquired with (FIG. 3A) 193-nm DUV-LA ESI and (FIG. 3BA) conventional ESI using a 50-μM vitamin $B_{12}$ solution in accordance with embodiments of the present disclosure.
Figure 3B:
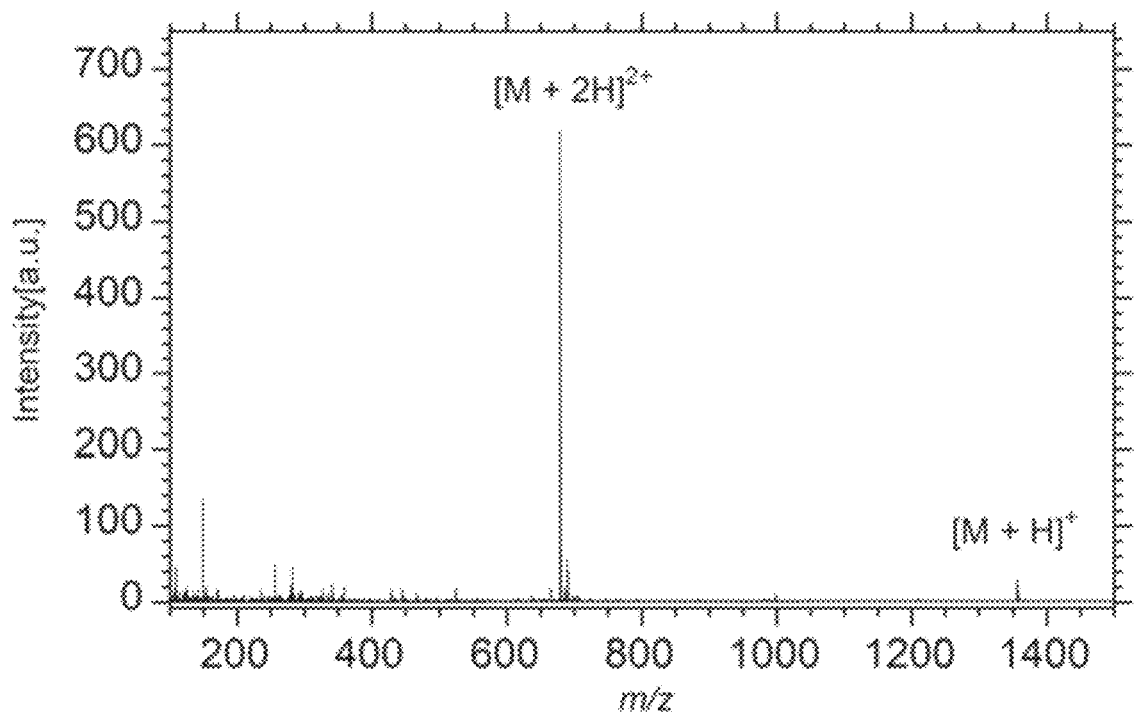

Vitamin $B_{12}$ has been used as a thermometer molecule with various ionization techniques.[33-36] Mass spectra of DUV-LAESI performed on a dried droplet sample of vitamin $B_{12}$ and conventional ESI infusion of the same solution are shown in FIGS. 3A-3B. FIG. 3A shows the mass spectrum obtained from ca. 8 nmol of vitamin $B_{12}$ using DUV-LAESI and FIG. 3B shows the mass spectrum obtained from infusion of a 50 μM solution of vitamin $B_{12}$. The base peak is the doubly-protonated molecule in both mass spectra and there is no substantial difference in observed peaks. A peak corresponding to the loss of the cyano group (doubly-charged) was detected in both the DUV-LAESI and ESI spectra, likely due to nozzle-skimmer dissociation. These results are consistent with those obtained by ESI and infrared laser ablation electrospray of vitamin $B_{12}$.[37] DUV-LAESI appears to be as soft an ionization technique as ESI and does not induce fragmentation of vitamin $B_{12}$ as observed with MALDI,[34-36] fast atom bombardment,[38] or plasma desorption mass spectrometry.[39]

Figure 4A:
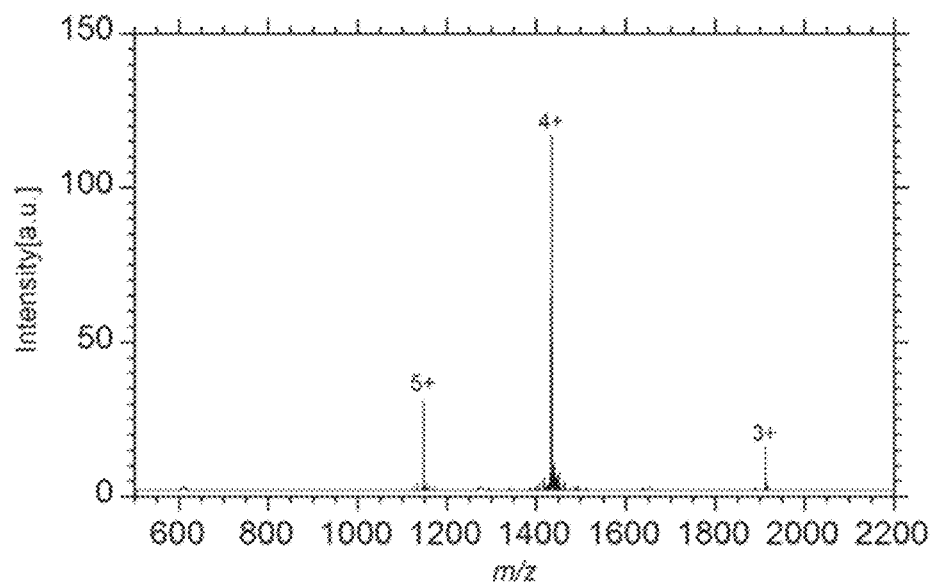
FIGS. 4A-4C provide mass spectra of (FIG. 4A) insulin.
Figure 4B:
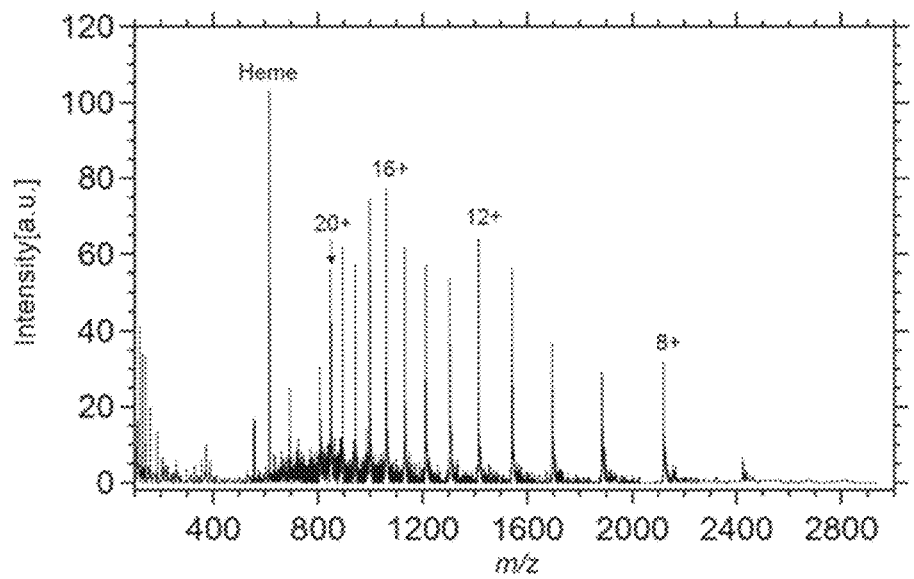
Figure 4C:
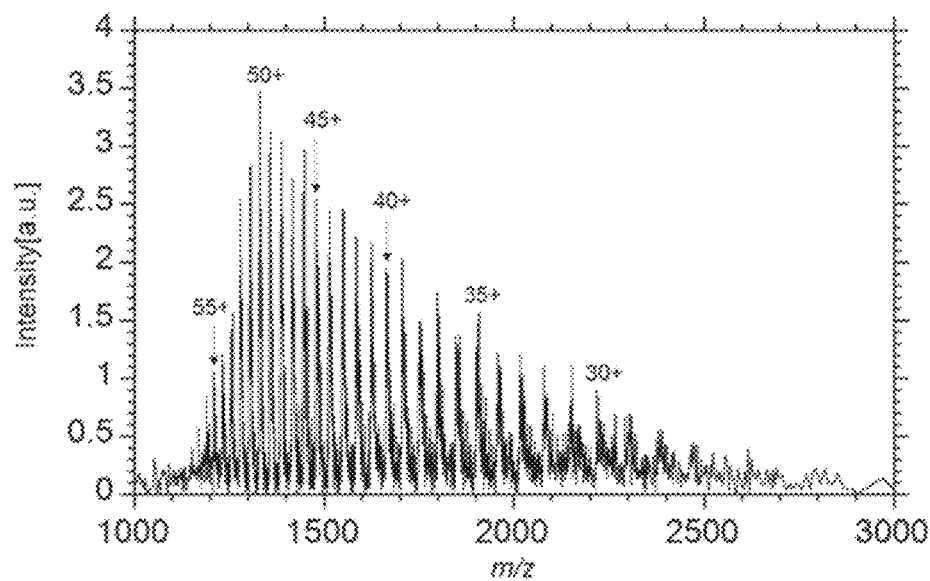
Figure 12A:
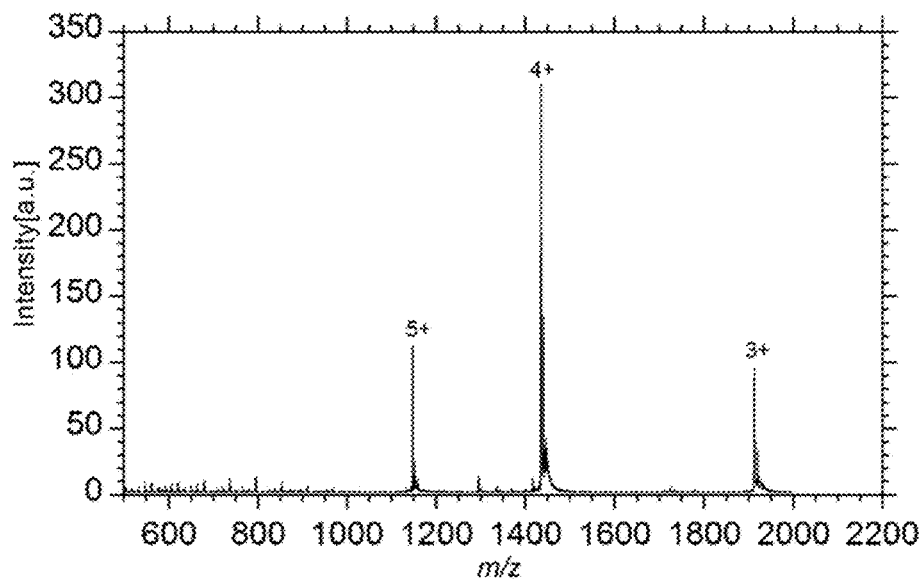
FIGS. 12A-12C provide representative ESI mass spectra of protein solutions containing FIG. 12A) 30 μM insulin (~5.7 kDa) FIG. 12B) 15 μM myoglobin (~17 kDa) and FIG. 12C) 15 μM bovine serum albumin (~66 kDa).
Figure 12B:
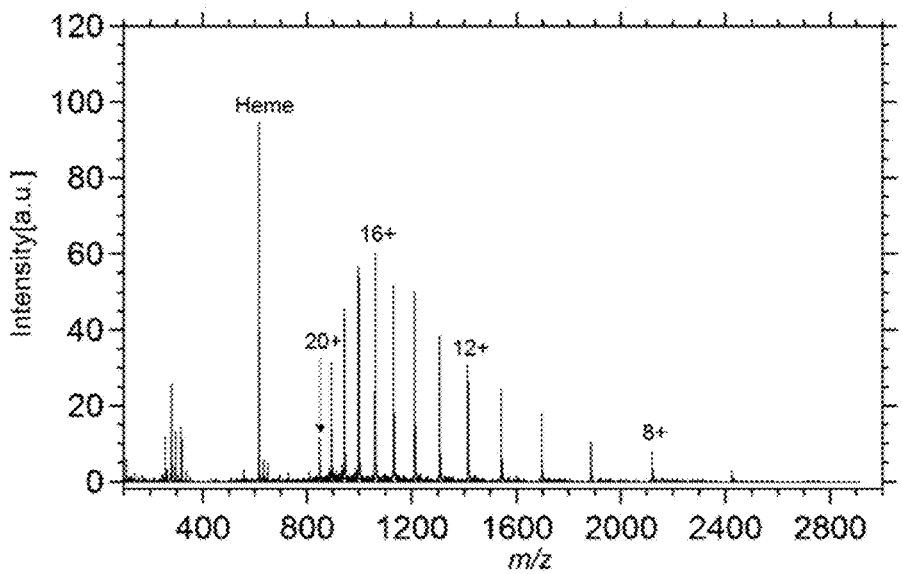
Figure 12C:
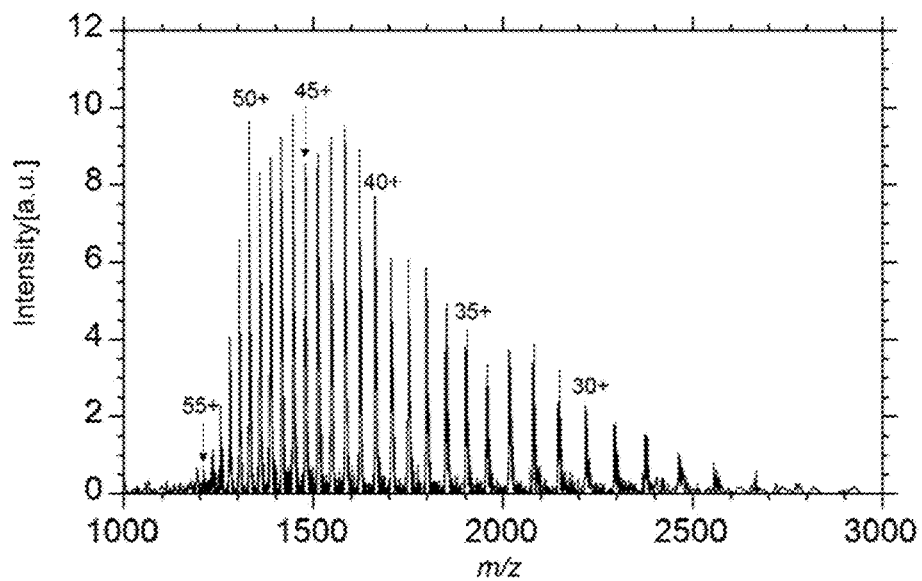
Figure 13A:
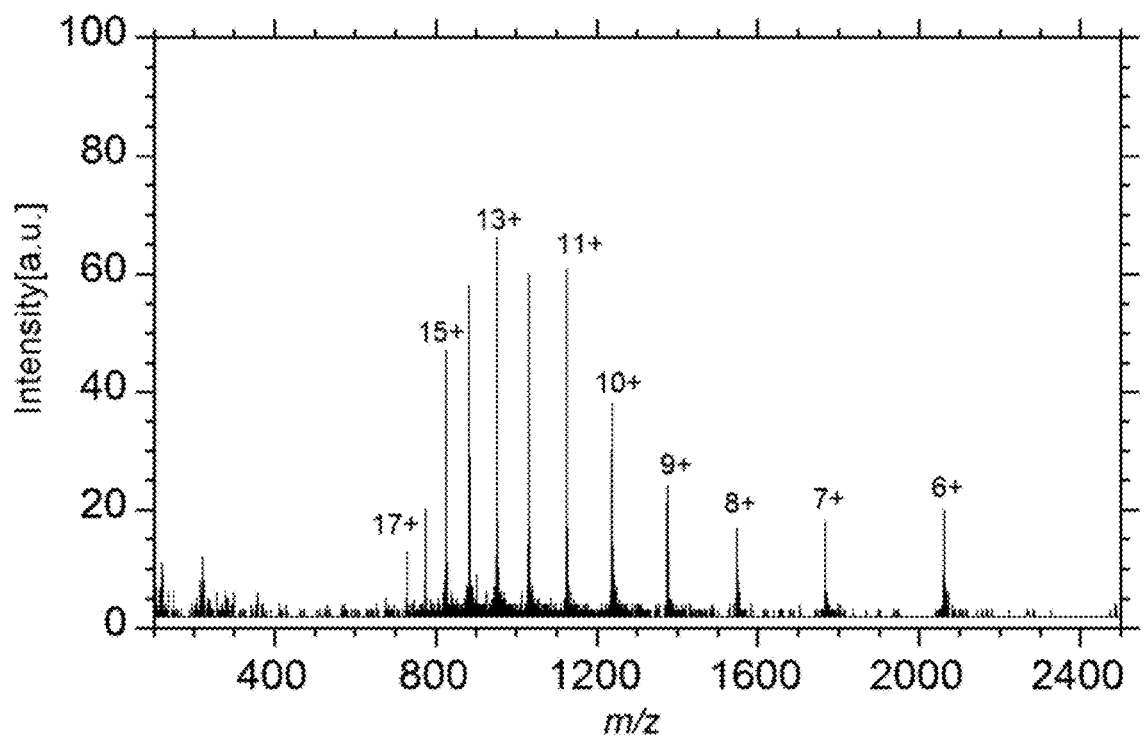
FIGS. 13A-13B are representative single acquisition DUV-LAESI mass spectra of FIG. 13A) cytochrome C (~12.3 kDa) and FIG. 13B) hemoglobin (~15.1 kDa) showing multiply charged protein peaks.
Figure 13B:
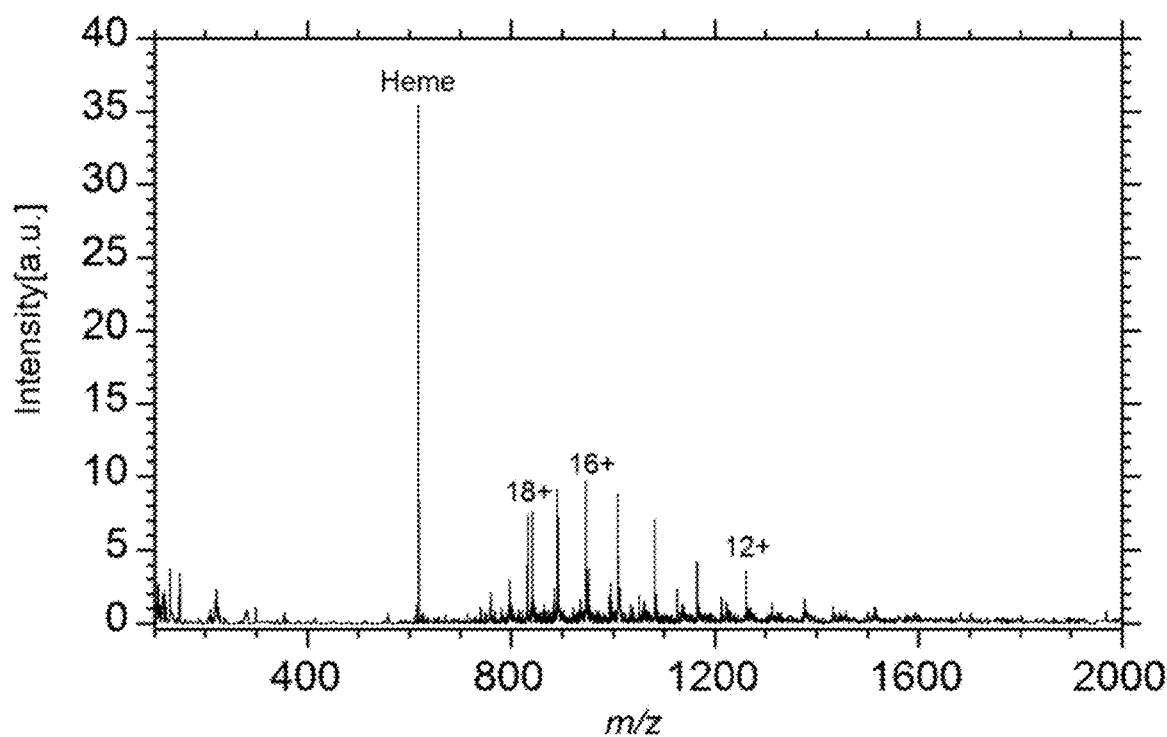

FIGS. 4A-4C show the spectra of proteins insulin, myoglobin and albumin obtained using DUV-LAESI from dried droplet samples containing 10 μL of 1 mg/ml solution of each protein. All proteins were detected as the multiply protonated intact molecule with no fragmentation detected and no significant difference in the mass spectra compared to conventional electrospray (FIGS. 12A-12B). FIG. 4B shows a mass spectrum obtained after ablation of myoglobin. The heme group was detected as a separate singly charged ion. Infusion of 5 μM myoglobin solution (FIGS. 12A-12B) produced a similar spectrum with the heme group lost as well. Similar results with the heme group detected as a singly charged ion has been observed following laser induced desorption and electrospray ionization of myoglobin.[40,41] Results were obtained using protein standards cytochrome c and hemoglobin; their respective spectra are shown in FIGS. 13A-13B.

Figure 5:
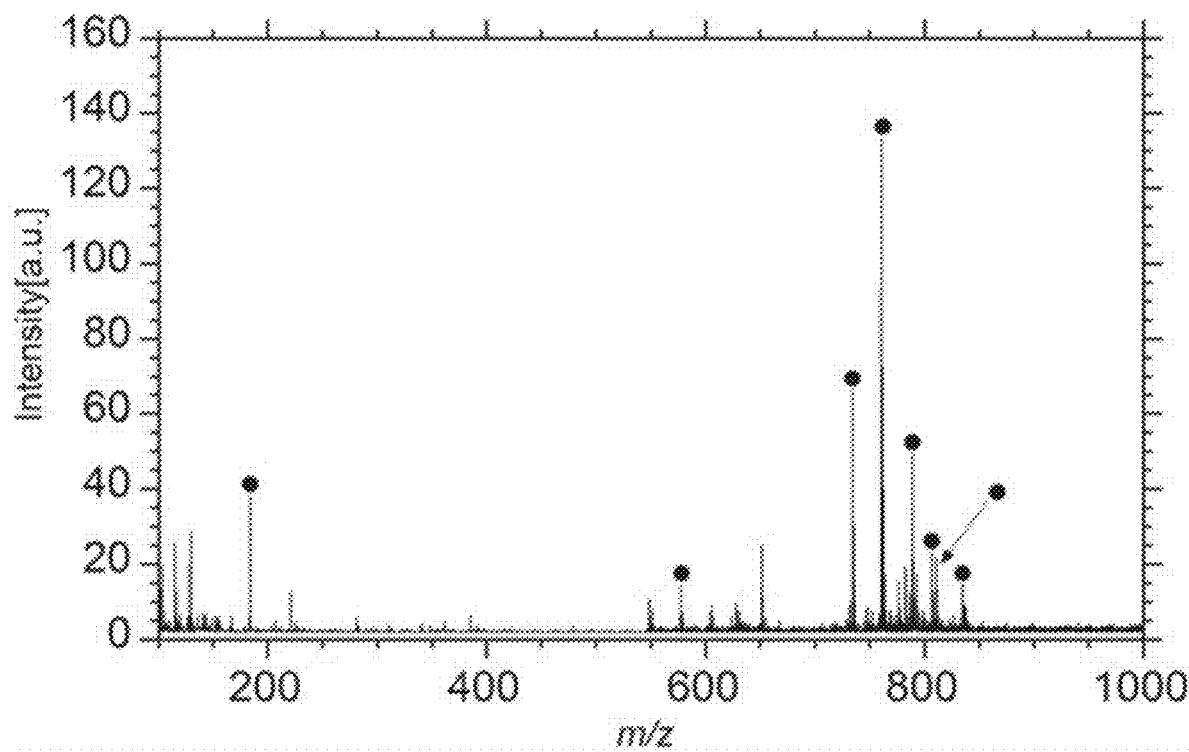
FIG. 5 is a representative DUV-LA-ESI mass spectrum according to embodiments of the present disclosure of a rat brain tissue, according to embodiments of the present disclosure, showing phosphocholine (PC) at m/z 184.1; PC(34:1) fragment at m/z 577.6; PC(32:0) at m/z 734.616; D, PC(34:1) at m/z 760.6; PC(36:1) at m/z 788.6; PC(38:6) at m/z 806.6; PC(38:4) at m/z 810.7; and H, PC(40:6) at m/z 834.7.

The DUV-LAESI approach was further tested using a rat brain tissue section mounted on a microscope slide. FIG. 5 shows a representative spectrum obtained from irradiation of an area in the frontal cortex region of the brain. Several peaks between 100-900 m/z were detected and identified as phospholipids based on searches performed on the Lipid MAPS database[42] using the recorded m/z. The dominant peak at m/z 760.638 corresponds to protonated PC (34:1) which is a major lipid in rat brain tissue.[43,44] The presence of the peak at m/z 577.564 is attributed to the loss of phosphocholine from the PC (34:1). Other prominent protonated ion peaks were observed at m/z values of 734.6, 788.6, 806.6, 810.7 and 834.7, corresponding to PC (32:0), PC (36:1), PC (36:6), PC (38:6), and PC (40:6), respectively. The detected phospholipids are consistent with those observed from rat brain tissue using matrix-assisted laser desorption (MALDI)[44] and laser ablation electrospray ionization (LAESI)[17] mass spectrometry. The phosphocholine ion at m/z 184.101 is typically detected during collision induced dissociation of phospholipids,[43,44] which further confirms the identity of the detected peaks. This peak is attributed to in source fragmentation in the orifice-skimmer region of the mass spectrometer that induces a CID-like dissociation.[45]

The potential absorbers of the 193 nm irradiation are the analyte, residual water in the sample or tissue, or the sample target. The absorption length of the pure protein (ca. 0.2 μm) and tissue (ca. 1 μm)[46-48] is small compared to the sample thickness (50 μm for tissue and ca. 1 μm for the protein films) which suggests that the sample target does not absorb the laser energy. Further, DUV-LAESI has been demonstrated with a range of target materials including glass microscope slides with similar results. Proteins have high absorption at 193 nm due to the π→π* electronic transition of peptide backbone near 190 nm,[48-51] and phosphatidylcholine molecules detected in the DUV-LAESI analysis of tissue (FIG. 5) absorb 193 nm radiation.[52] Thus, the analyte itself may absorb a significant fraction of the laser energy. Whereas the irradiated molecules may fragment, it may be possible that their energy absorption leads to material ejection as a form of "sacrificial matrix", which has been suggested as a mechanism of IR ablation.[53] Water at room temperature has an absorption coefficient of about 0.1 $cm^{-1}$ at 193 nm, but when heated the peak absorption shifts from its peak at 163 nm to longer wavelengths due to disruption of hydrogen bonding.[54] When heated to a volumetric energy density of 3000 $J/m^3$ the 193 nm absorption increases to 12,000 $cm^{-1}$. This effect is similar to the thermal bootstrap effect that has been observed for infrared laser ablation of biomolecules.[55-57] As the system is heated, the absorption increases leading to greater energy absorption. Thus, in addition to analyte absorption, absorption of the laser energy by water may be a factor in the ablation process.

The 8 ns pulse width of the 193 nm laser is shorter than the time for thermal diffusion which is on the microsecond time scale for μm optical penetration depths.[46] In this case, the system is in the thermal confinement regime.[58,59] The system will be in stress confinement if the optical penetration depth is greater than the distance that a pressure wave travels during the laser pulse. The characteristic time for stress confinement is approximately 20 ns in tissue at 193 nm.[46] A large increase in optical absorption at 193 nm due to thermal bootstrap could move the system outside of the pressure confined regime, resulting in less stress in the sample and a less violent ejection of material compared to the infrared. In addition, 193 nm ablation can lead to bond breakage and bubble nucleation from the gases produced by the photochemical decomposition of the sample.[46] These gases can reduce the effects of phase explosion by providing nucleation sites and reduce the effects of superheating and volumetric boiling. Thus deep-UV ablation can be a physically less violent process compared to mid-IR ablation.

The lack of biomolecule fragmentation observed suggests that the mechanism of material ejection is based on absorption of the laser energy by some of the biomolecules in the sample that photochemically decompose to form gases that serve as nucleation sites for boiling. There may be an additional photothermal component assisted by the strong absorption of water and a UV thermal bootstrap effect. It is likely that the plume of ejected material contains a large quantity of small neutral particulate[60,61] that may efficiently merge with the spray of charged electrospray particles. The low optical penetration depth of the deep UV laser leads to the production of smaller particles than other wavelengths.[62] A large number of small particles formed in this manner would be anticipated to efficiently merge with the electrospray plume in the fused-droplet mechanism proposed for ELDI[18] and LAESI.[21]

CONCLUSIONS

Laser ablation coupled with electrospray ionization of peptides and proteins was accomplished using 193 nm deep ultraviolet laser ablation. The biomolecules were observed intact with mass spectra indistinguishable from conventional electrospray. No fragmentation was observed for vitamin $B_{12}$ in contrast to that observed in matrix-assisted laser desorption ionization. Laser ablation electrospray ionization of rat brain tissue at 193 nm allowed the detection of intact phospholipids directly from the sample. The mechanism of ablation is postulated to involve the absorption of laser energy by the analyte molecules themselves or by water in the sample. Absorption by the biomolecules may involve a sacrificial matrix mechanism in which some of the biomolecules absorbing the laser energy are fragmented but the absorbed laser energy expels a large number of intact biomolecules that are ionized and detected. A thermal bootstrap effect that has been previously reported to shift the water electronic absorption into resonance with the 193 nm laser may be an additional component of the laser energy absorption. Deep ultraviolet laser ablation provides opportunities to create ions under ambient conditions with micrometer spatial resolution for mass spectrometry with conventional optics and without the use of a matrix.

EXAMPLE 1 REFERENCES

[1] R. G. Cooks, Z. Ouyang, Z. Takats, J. M. Wiseman. Ambient mass spectrometry. *Science.* 2006, 311, 1566-1570.
[2] M.-Z. Huang, C.-H. Yuan, S.-C. Cheng, Y.-T. Cho, J. Shiea. Ambient ionization mass spectrometry. *Annu. Rev. Anal. Chem.* 2010, 3, 43-65.
[3] C. Wu, A. L. Dill, L. S. Eberlin, R. G. Cooks, D. R. Ifa. Mass spectrometry imaging under ambient conditions. *Mass Spectrom. Rev.* 2013, 32, 218-243.
[4] C.-C. Hsu, P. C. Dorrestein. Visualizing life with ambient mass spectrometry. *Curr. Opin. Biotechnol.* 2015, 31, 24-34.
[5] Z. Takats, J. M. Wiseman, B. Gologan, R. G. Cooks. Mass spectrometry sampling under ambient conditions with desorption electrospray ionization. *Science.* 2004, 306, 471-473.
[6] R. B. Cody, J. A. Laramée, H. D. Durst. Versatile new ion source for the analysis of materials in open air under ambient conditions. *Anal. Chem.* 2005, 77, 2297-2302.
[7] V. V. Laiko, M. A. Baldwin, A. L. Burlingame. Atmospheric pressure matrix-assisted laser desorption/ionization mass spectrometry. *Anal. Chem.* 2000, 72, 652-657.
[8] V. V. Laiko, N. I. Taranenko, V. D. Berkout, M. A. Yakshin, C. R. Prasad, H. S. Lee, V. M. Doroshenko. Desorption/ionization of biomolecules from aqueous solutions at atmospheric pressure using an infrared laser at 3 µm. *J. Am. Soc. Mass. Spectrom.* 2002, 13, 354-361.
[9] Y. Li, B. Shrestha, A. Vertes. Atmospheric pressure molecular imaging by infrared MALDI mass spectrometry. *Anal. Chem.* 2007, 79, 523-532.
[10] Y. Coello, A. D. Jones, T. C. Gunaratne, M. Dantus. Atmospheric pressure femtosecond laser imaging mass spectrometry. *Anal. Chem.* 2010, 82, 2753-2758.
[11] A. L. Gray. Solid sample introduction by laser ablation for inductively coupled plasma source mass spectrometry. *Analyst.* 1985, 110, 551-556.
[12] R. E. Russo, X. Mao, J. J. Gonzalez, S. S. Mao. Femtosecond laser ablation ICP-MS. *J. Anal. At. Spectrom.* 2002, 17, 1072-1075.
[13] R. Russo, X. Mao, J. Gonzalez, V. Zorba, J. Yoo. Laser ablation in analytical chemistry. *Anal. Chem.* 2013, 85, 6162-6177.
[14] J. J. Coon, K. J. McHale, W. Harrison. Atmospheric pressure laser desorption/chemical ionization mass spectrometry: a new ionization method based on existing themes. *Rapid Commun. Mass Spectrom.* 2002, 16, 681-685.
[15] L. Nyadong, J. P. Quinn, C. S. Hsu, C. L. Hendrickson, R. P. Rodgers, A. G. Marshall. Atmospheric pressure laser-induced acoustic desorption chemical ionization mass spectrometry for analysis of saturated hydrocarbons. *Anal. Chem.* 2012, 84, 7131-7137.
[16] A. Vaikkinen, B. Shrestha, T. J. Kauppila, A. Vertes, R. Kostiainen. Infrared laser ablation atmospheric pressure photoionization mass spectrometry. *Anal. Chem.* 2012, 84, 1630-1636.
[17] P. Nemes, A. S. Woods, A. Vertes. Simultaneous imaging of small metabolites and lipids in rat brain tissues at atmospheric pressure by laser ablation electrospray ionization mass spectrometry. *Anal. Chem.* 2010, 82, 982-988.
[18] J. Shiea, M. Z. Huang, H. J. HSu, C. Y. Lee, C. H. Yuan, I. Beech, J. Sunner. Electrospray-assisted laser desorption/ionization mass spectrometry for direct ambient analysis of solids. *Rapid Commun. Mass Spectrom.* 2005, 19, 3701-3704.
[19] J. S. Sampson, A. M. Hawkridge, D. C. Muddiman. Generation and detection of multiply-charged peptides and proteins by matrix-assisted laser desorption electrospray ionization (MALDESI) Fourier transform ion cyclotron resonance mass spectrometry. *J. Am. Soc. Mass. Spectrom.* 2006, 17, 1712-1716.

[20] J. J. Brady, E. J. Judge, R. J. Levis. Mass spectrometry of intact neutral macromolecules using intense non-resonant femtosecond laser vaporization with electrospray post-ionization. *Rapid Commun. Mass Spectrom.* 2009, 23, 3151-3157.

[21] P. Nemes, A. Vertes. Laser ablation electrospray ionization for atmospheric pressure, in vivo, and imaging mass spectrometry. *Anal. Chem.* 2007, 79, 8098-8106.

[22] Y. H. Rezenom, J. Dong, K. K. Murray. Infrared laser-assisted desorption electrospray ionization mass spectrometry. *Analyst.* 2008, 133, 226-232.

[23] J. S. Sampson, K. K. Murray, D. C. Muddiman. Intact and top-down characterization of biomolecules and direct analysis using infrared matrix-assisted laser desorption electrospray ionization coupled to FT-ICR mass spectrometry. *J. Am. Soc. Mass. Spectrom.* 2009, 20, 667-673.

[24] A. S. Galhena, G. A. Harris, L. Nyadong, K. K. Murray, F. M. Fernandez. Small molecule ambient mass spectrometry imaging by infrared laser ablation metastable-induced chemical ionization. *Anal. Chem.* 2010, 82, 2178-2181.

[25] E. J. Judge, J. J. Brady, P. E. Barbano, R. J. Levis. Nonresonant femtosecond laser vaporization with electrospray postionization for ex vivo plant tissue typing using compressive linear classification. *Anal. Chem.* 2011, 83, 2145-2151.

[26] J. Zou, F. Talbot, A. Tata, L. Ermini, K. Franjic, M. Ventura, J. Zheng, H. Ginsberg, M. Post, D. R. Ifa. Ambient mass spectrometry imaging with picosecond infrared laser ablation electrospray ionization (PIR-LAESI). *Anal. Chem.* 2015, 87, 12071-12079.

[27] K. L. Fowble, K. Teramoto, R. B. Cody, D. Edwards, D. Guarrera, R. A. Musah. Development of "Laser Ablation Direct Analysis in Real Time Imaging" Mass Spectrometry: Application to Spatial Distribution Mapping of Metabolites Along the Biosynthetic Cascade Leading to Synthesis of Atropine and Scopolamine in Plant Tissue. *Anal. Chem.* 2017, 89, 3421-3429.

[28] I. Kuznetsov, J. Filevich, F. Dong, M. Woolston, W. Chao, E. H. Anderson, E. R. Bernstein, D. C. Crick, J. J. Rocca, C. S. Menoni. Three-dimensional nanoscale molecular imaging by extreme ultraviolet laser ablation mass spectrometry. *Nat. Commun.* 2015, 6, 6944.

[29] H. A. Wang, D. Grolimund, C. Giesen, C. N. Borca, J. R. Shaw-Stewart, B. Bodenmiller, D. Günther. Fast chemical imaging at high spatial resolution by laser ablation inductively coupled plasma mass spectrometry. *Anal. Chem.* 2013, 85, 10107-10116.

[30] C. Giesen, H. A. Wang, D. Schapiro, N. Zivanovic, A. Jacobs, B. Hattendorf, P. J. Schiffler, D. Grolimund, J. M. Buhmann, S. Brandt. Highly multiplexed imaging of tumor tissues with subcellular resolution by mass cytometry. *Nature Methods.* 2014, 11, 417.

[31] C. Geertsen, A. Briand, F. Chartier, J.-L. Lacour, P. Mauchien, S. Sjöström, J.-M. Mermet. Comparison between infrared and ultraviolet laser ablation at atmospheric pressure—implications for solid sampling inductively coupled plasma spectrometry. *J. Anal. At. Spectrom.* 1994, 9, 17-22.

[32] R. Srinivasan. Ablation of polymers and biological tissue by ultraviolet lasers. *Science.* 1986, 234, 559-565.

[33] M. Castro, D. Russell. Cesium ion desorption ionization with Fourier transform mass spectrometry (FTMS). *Anal. Chem.* 1984, 56, 578-581.

[34] H. M. Schiebel, H. R. Schulten. Soft ionization of biomolecules: A comparison of ten ionization methods for corrins and vitamin B12. *Mass Spectrom. Rev.* 1986, 5, 249-311.

[35] G. R. Kinsel, L. M. Preston, D. H. Russell. Fragmentation of vitamin B12 during 337 nm matrix-assisted laser desorption ionization. *Biological mass spectrometry.* 1994, 23, 205-211.

[36] L. He, G. Wei, K. K. Murraycor. Fragmentation of vitamin B12 in aerosol matrix-assisted laser desorption ionization. *J. Am. Soc. Mass. Spectrom.* 1997, 8, 140-147.

[37] P. Nemes, H. Huang, A. Vertes. Internal energy deposition and ion fragmentation in atmospheric-pressure mid-infrared laser ablation electrospray ionization. *PCCP.* 2012, 14, 2501-2507.

[38] M. Barber, R. S. Bordoli, R. D. Sedgwick, A. N. Tyler. Fast atom bombardment mass spectrometry of cobalamines. *Biological Mass Spectrometry.* 1981, 8, 492-495.

[39] J. Blankenship, M. VanStipdonk, E. Schweikert. Matrix effects on the fragmentation of vitamin B12 in plasma desorption mass spectrometry. *Rapid Commun. Mass Spectrom.* 1997, 11, 143-147.

[40] V. Golovlev, S. Allman, W. Garrett, N. Taranenko, C. Chen. Laser-induced acoustic desorption. *Int. J. Mass Spectrom. Ion Processes.* 1997, 169, 69-78.

[41] S.-C. Cheng, T.-L. Cheng, H.-C. Chang, J. Shiea. Using laser-induced acoustic desorption/electrospray ionization mass spectrometry to characterize small organic and large biological compounds in the solid state and in solution under ambient conditions. *Anal. Chem.* 2008, 81, 868-874.

[42] E. Fahy, M. Sud, D. Cotter, S. Subramaniam. LIPID MAPS online tools for lipid research. *Nucleic Acids Res.* 2007, 35, W606-W612.

[43] J. A. Hankin, R. M. Barkley, R. C. Murphy. Sublimation as a method of matrix application for mass spectrometric imaging. *J. Am. Soc. Mass. Spectrom.* 2007, 18, 1646-1652.

[44] S. N. Jackson, H.-Y. J. Wang, A. S. Woods. In situ structural characterization of phosphatidylcholines in brain tissue using MALDI-MS/MS. *J. Am. Soc. Mass. Spectrom.* 2005, 16, 2052-2056.

[45] B. B. Schneider, D. D. Chen. Collision-Induced Dissociation of Ions within the Orifice-Skimmer Region of an Electrospray Mass Spectrometer. *Anal. Chem.* 2000, 72, 791-799.

[46] A. Vogel, V. Venugopalan. Mechanisms of pulsed laser ablation of biological tissues. *Chem. Rev.* 2003, 103, 577-644.

[47] A. D. Yablon, N. S. Nishioka, B. B. Mikić, V. Venugopalan. Measurement of tissue absorption coefficients by use of interferometric photothermal spectroscopy. *Appl. Opt.* 1999, 38, 1259-1272.

[48] B. T. Fisher, D. W. Hahn. Measurement of small-signal absorption coefficient and absorption cross section of collagen for 193-nm excimer laser light and the role of collagen in tissue ablation. *Appl. Opt.* 2004, 43, 5443-5451.

[49] V. I. Dodero, Z. B. Quirolo, M. A. Sequeira. Biomolecular studies by circular dichroism. *Frontiers in Bioscience.* 2011, 16, 61-73.

[50] D. Wetlaufer. Book Ultraviolet spectra of proteins and amino acids. Elsevier. 1963. 303-390.

[51] A. Lembares, X.-H. Hu, G. W. Kalmus. Absorption spectra of corneas in the far ultraviolet region. *Invest. Ophthalmol. Vis. Sci.* 1997, 38, 1283-1287.

[52] D. R. Klein, J. S. Brodbelt. Structural characterization of phosphatidylcholines using 193 nm ultraviolet photodissociation mass spectrometry. *Anal. Chem.* 2017, 89, 1516-1522.

[53] M. W. Little, J. Laboy, K. K. Murray. Wavelength dependence of soft infrared laser desorption and ionization. *The Journal of Physical Chemistry.* 2007, 111, 1412-1416.

[54] P. T. Staveteig, J. T. Walsh. Dynamic 193-nm optical properties of water. *Appl. Opt.* 1996, 35, 3392-3403.

[55] R. Cramer, R. F. Haglund Jr, F. Hillenkamp. Matrix-assisted laser desorption and ionization in the O—H and C=O absorption bands of aliphatic and aromatic matrices: dependence on laser wavelength and temporal beam profile. *Int. J. Mass Spectrom. Ion Processes.* 1997, 169, 51-67.

[56] J. D. Sheffer, K. K. Murray. Infrared matrix-assisted laser desorption/ionization using OH, NH and CH vibrational absorption. *Rapid Commun. Mass Spectrom.* 1998, 12, 1685-1690.

[57] C. Menzel, K. Dreisewerd, S. Berkenkamp, F. Hillenkamp. Mechanisms of energy deposition in infrared matrix-assisted laser desorption/ionization mass spectrometry. *Int. J. Mass spectrom.* 2001, 207, 73-96.

[58] L. V. Zhigilei, B. J. Garrison. Microscopic mechanisms of laser ablation of organic solids in the thermal and stress confinement irradiation regimes. *J. Appl. Phys.* 2000, 88, 1281-1298.

[59] A. Aesa, C. Walton. 193 nm ArF laser ablation and patterning of chitosan thin films. *Appl. Phys. A.* 2018, 124, 444.

[60] T. Musapelo, K. K. Murray. Particle formation in ambient MALDI plumes. *Anal. Chem.* 2011, 83, 6601-6608.

[61] F. Cao, F. Donnarumma, K. K. Murray. Particle size measurement from infrared laser ablation of tissue. *Analyst.* 2016, 141, 183-190.

[62] I. Apitz, A. Vogel. Material ejection in nanosecond Er:YAG laser ablation of water, liver, and skin. *Appl. Phys. A.* 2005, 81, 329-338.

Example 2: Precision Tissue Microdissection Using Deep Ultraviolet Laser Ablation The deep-UV laser ablation sample capture system of the present disclosure can be demonstrated using mouse brain tissue samples. Material will be collected with the DUV-LA system described above and these results will be compared with laser microdissected tissue.

Figure 6:
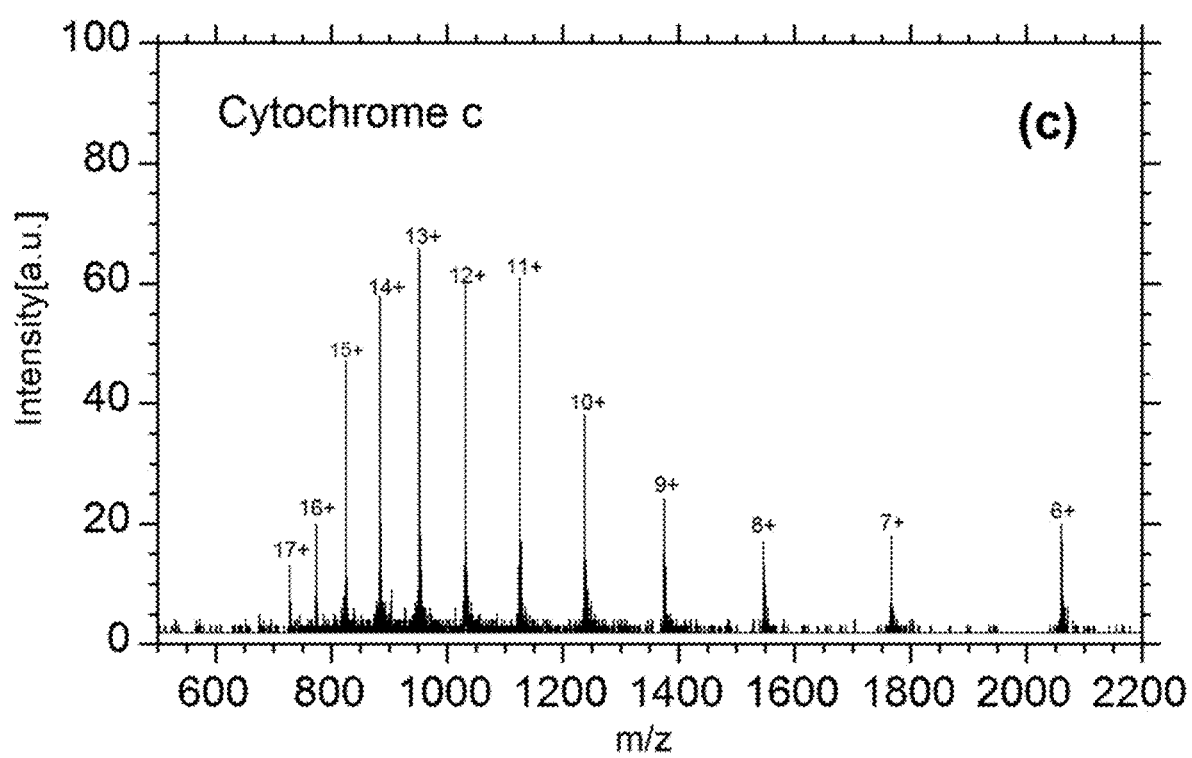
FIG. 6 provides a mass spectrum, demonstrating that intact proteins can be sampled with the DUV-LA technology described herein.

The DUV-LA instrument has been successfully used to demonstrate protein ablation with no fragmentation observed by on-line mass spectrometry. Sections of rat brain tissue were sampled and the constituent lipids were analyzed. A mass spectrum of an intact protein is shown in FIG. 6. The laser wavelength was 193 nm and the proteins were post-ionized by an electrospray of methanol. These mass spectra demonstrate that proteins can be ablated and captured intact using the 193 nm laser.

Tissue sampling protocols are currently in place[3] and samples obtained from LSU School of Veterinary medicine using a currently approved IACUC protocol. A glass microscope slide with a rat brain tissue section is placed on microscope sample stage prior to the experiments. The microscope images of the area of interest are obtained prior to the ablation experiments for comparison. Material is laser ablated from one or more spots on the tissue and the ablated material is captured on the suspended wire. The material is transported from the stage as described above and washed into a 96 well plate using 2 µL of PE buffer solution. Transfer is repeated to obtain the desired number of samples and negative controls are prepared by ablating and collecting from tissue-free portions of the slide.

Protein sequencing of the laser ablated and control microdissected tissue can be performed in a mass spectrometry facility and estimates of the total protein concentration made with such as a Bradford colorimetric assay. Calibration curves can be obtained using bovine serum albumin standards. Quantification can be performed using such as a Thermo Scientific Nanodrop Spectrophotometer. Tandem mass spectrometry protein sequencing can be performed using such as a Bruker Amazon ion trap mass spectrometer and liquid chromatography system with C18 column. Identification can be performed using such as a Bruker BioTools and PeptideShaker on a server, along with identification of MALDI MS/MS spectra and peptide fingerprinting analysis.

Next generation DNA sequencing of the microdissected tissue can be performed using standard protocols. For multiple displacement amplification in this example, the collected material was transferred to a PCR tube containing PBS solution. Amplification was accomplished using a REPLI-g Single Cell Kit (QIAGEN). The mixture was incubated with REPLI-g sc Master Mix at 30° C. for 16 h and terminated at 65° C. for 10 min. The amplified DNA products were stored at –20° C. Whole genome amplified DNA was purified using a QIAquick PCR Purification Kit. The mixture was transferred to a vacuum-dried 96 well plate containing PE buffer and proceeds to the DNA purification according to the manufacturer's protocol. The mixture was flowed through a silica-gel membrane and washed using Buffer PE buffer. Buffer EB was used to elute target DNA. Industry standard quality benchmarks can be used for next-generation DNA sequencing. The minimum ablated volume required for small volume sequencing will be determined and a comparison of bulk laser microdissection-based sequencing with spatially resolved sequencing formulated.

Example 3: Two-Laser Ablation Electrospray Ionization Mass Spectrometry

The goal of the present example was to improve spatial resolution and efficiency of laser ablation electrospray ionization mass spectrometry for tissue imaging. While the IR laser is efficient at ablation, it is not useful for small particle formation. Small particles are needed for efficient merging with electrospray. It was discovered that deep UV as described in the examples above could be combined with IR laser for LAESI. No matrix was needed and no fragmentation occurred.

Figure 7A:
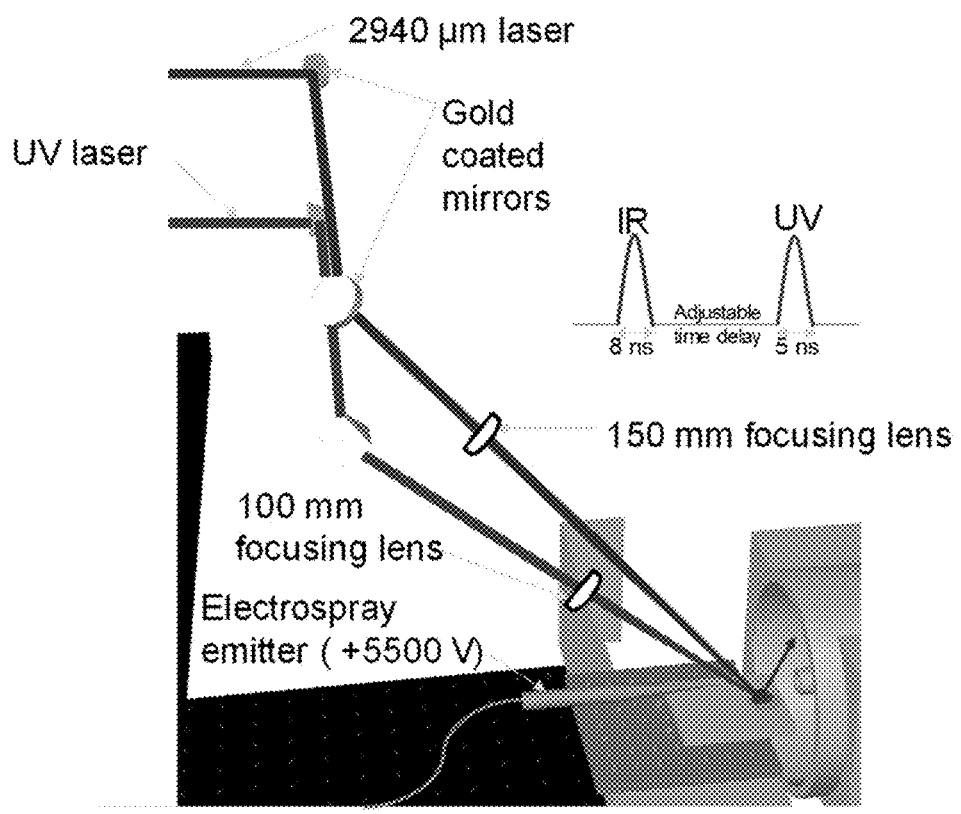
FIGS. 7A-7B are embodiments of a dual laser infrared/ultraviolet LAESI in accordance with the present disclosure.
Figure 7B:
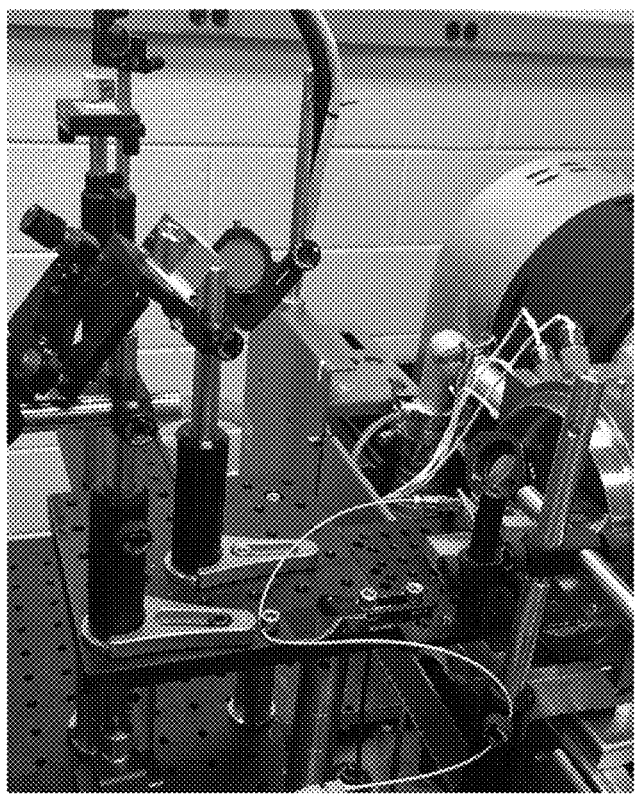

Embodiments of the two-laser system, or IR/UV LAESI device, of the present example are shown in FIGS. 7A and 7B. The system includes both a UV laser and an IR laser. The UV laser can be a frequency quadrupled Nd:YAG laser at 266 nm. A fifth harmonic Nd:YAG at 213 nm could also be used. The UV laser could also be an excimer laser tunable to 157 nm, 193 nm and 248 nm.

A time delay of the lasers can be adjusted using a pulse and delay generator to externally control the firing of the lasers. The two lasers can be fired with a nanosecond to microsecond delay between them and the delay is user selectable. The IR laser in the present example was a 2940 µm laser. A coated mirror is associated with each of the lasers. Each laser is focused through a focusing lens. In the present example, a 100 mm lens for the UV laser and a 150 mm lens for the IR laser were employed, but other lenses could be substituted as can be envisioned by one of ordinary skill in the art. The system also includes an electrospray emitter. In the present example, a +5500 V emitter was used. Other emitters could be used as envisioned by one of skill in the art.

The UV laser can be configured to operate in two modes, depending upon the desired use. In the "heat" mode, IR-UV can be used for increased efficiency. The UV laser (266 nm Nd:YAG) breaks up tissue structure for IR ablation. Alternatively, the IR laser heats tissue for UV ablation (193 nm) in the "tenderize mode". In this mode UV-IR is used to disrupt connective tissue material for efficient IR ablation.

One advantage of using a dual laser device is that the UV laser can be focused to a smaller spot size which is diffraction limited to approximately one-half the laser wavelength or greater. Thus, the UV spot can be focused to 15× smaller spot with corresponding optics compared to the IR laser. The theoretical smallest spot achievable with the lasers are ~1.5 µm for 2940 nm lasers and ~0.1 µm for the 193 nm laser.

Samples were prepared for ablation using deep UV LAESI (193 nm). 10 µL each of myoglobin and albumin were sampled, as was 50 µm of rat brain tissue (FIGS. 8A-8D). Mass spectra results showed that no fragmentation occurred and no added matrix was needed. Peaks were present for lipids in tissue (phosphocholine, FIG. 8C), and analysis of large proteins (BSA, ~66 kDa) was possible.

Figure 9A:
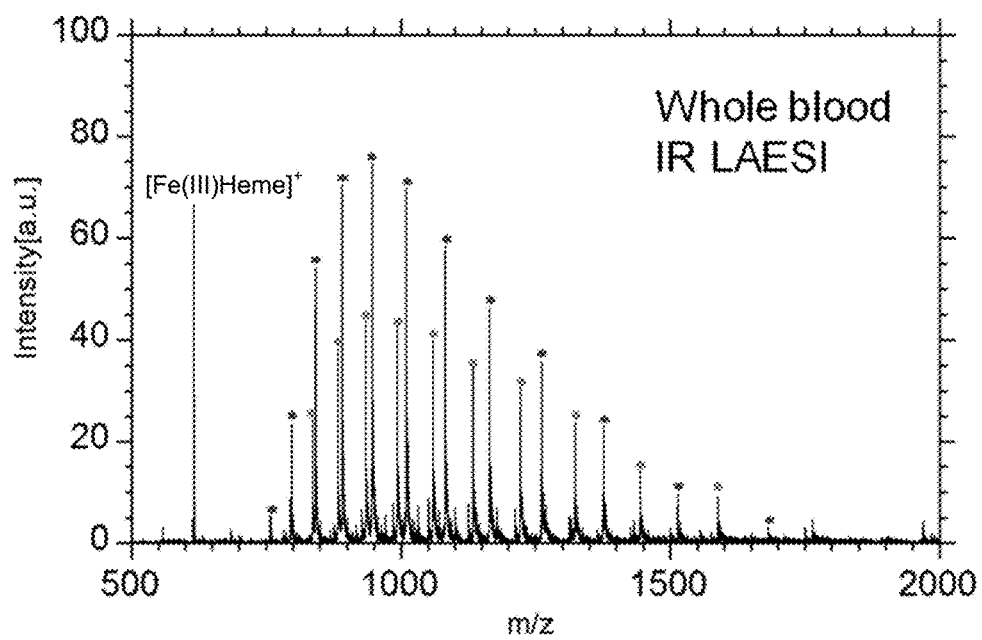
FIGS. 9A-9D are mass spectra of biological material after IR and IR/UV LAESI according to embodiments of the present disclosure (FIG. 9A, whole blood after IR LAESI.
Figure 9B:
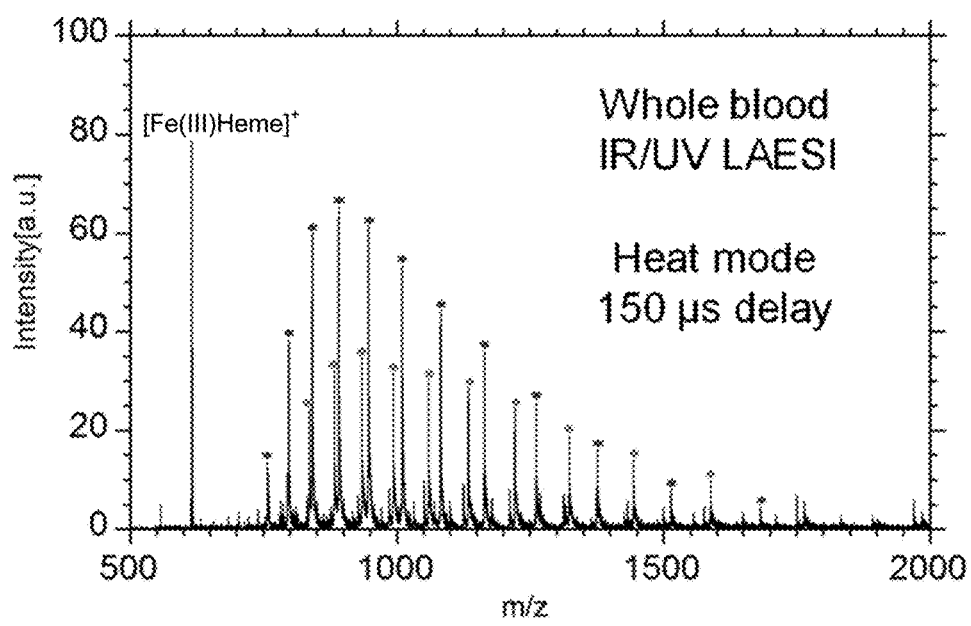
Figure 9C:
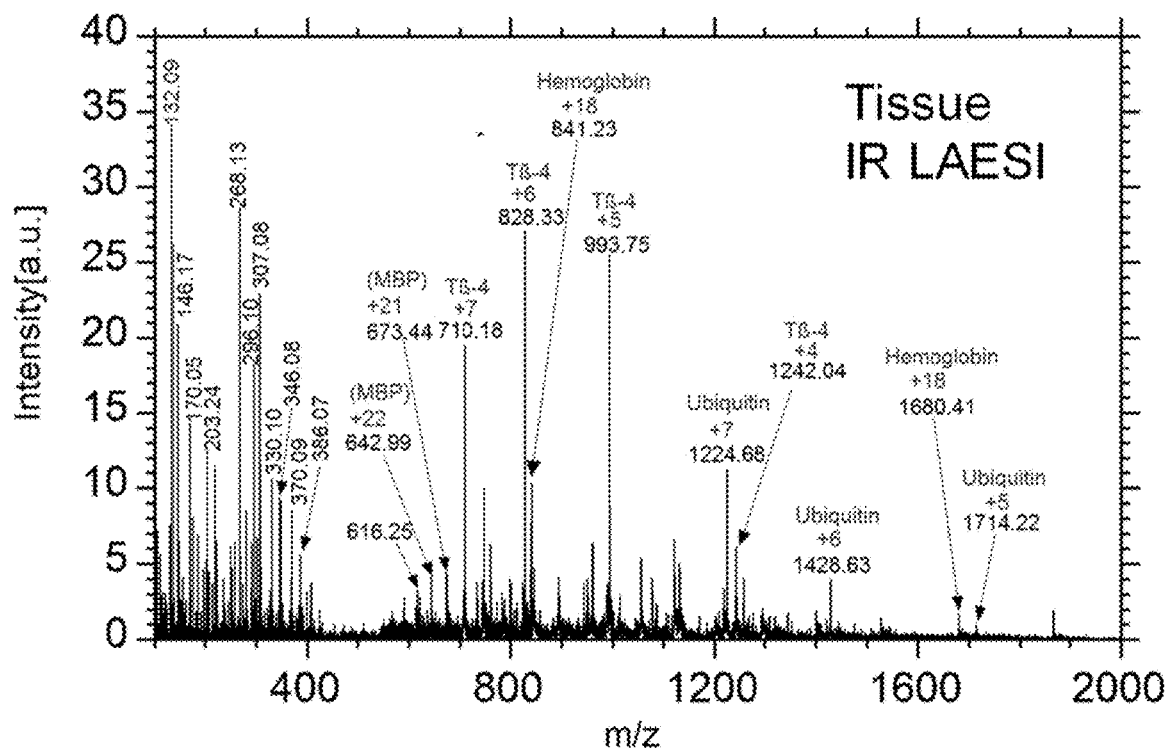
Figure 9D:
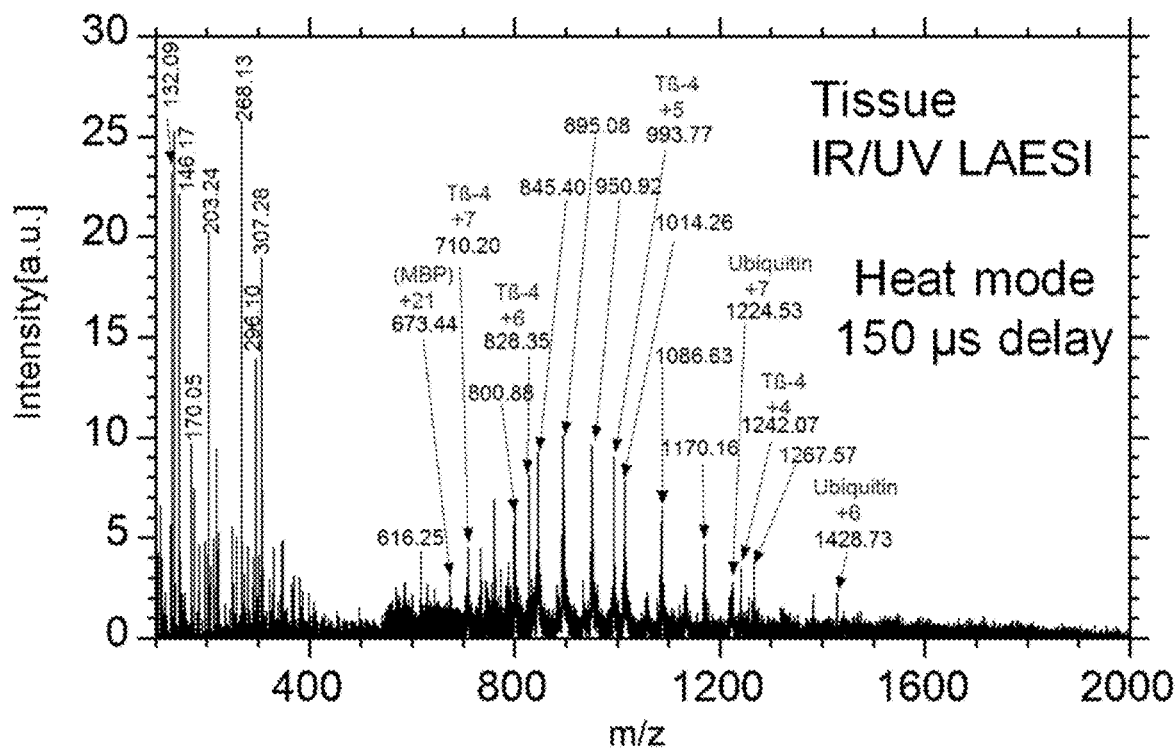

For testing of the IR/UV LAESI, whole blood and tissue samples were analyzed using IR LAESI and IR/UV LAESI in heat mode with a 150 µs delay (FIGS. 9A-9D). In this example, 2940 IR and 266 UV were used. In the heat mode, the IR laser is used to heat with the UV laser used to ablate in a delayed pulse. Both sampling methods were successful, and it was shown that irradiating with the UV laser does not cause fragmentation. Unexpectedly, the use of the dual laser IR/UV LAESI resulted in the identification of a new protein (MW 15198.8±0.5 Da) from the tissue sample (FIG. 9D).

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. An ablation device comprising:
a deep UV laser;
an electrospray ion source having an electrospray emitter;
a focusing lens; and
a sample target.

2. The device of claim 1, wherein the deep UV laser is a pulsed nanosecond 193-nm laser.

3. The device of claim 1, where the device is coupled to a LAESI or ELDI system.

4. The device of claim 1, wherein the device further comprises an optical microscope and a collection and transportation module that will interface with standard sequencing units.

5. A dual-laser ablation device, comprising:
a first laser and a second laser with adjustable firing time delay;
a first focusing lens and a second focusing lens; and
an electrospray ion source having an electrospray emitter.

6. The device of claim 5, wherein the first laser is a UV laser and a beam of the UV laser is directed through the first focusing lens, and wherein the second laser is an IR laser and a beam of the IR laser is directed through the second focusing lens.

7. The device of claim 5, wherein the first laser is selected from a 193 nm UV laser or a 266 nm UV laser.

8. The device of claim 5, wherein the second laser is a 2940 µm IR laser.

9. The device of claim 5, further comprising a first and a second mirror, wherein the mirrors direct the beams of the first and second lasers through the first and second lenses, respectively.

10. A method for laser ablation of biomolecules, comprising:
applying a sample to a target;
directing a beam of at least one deep UV laser at the sample; and
directing an electrospray at the laser beam; and
wherein the directing results in protonated sample molecules.

11. The method of claim 10, wherein the at least one deep UV laser can be a 193 nm laser, a 266 nm laser, or a combination thereof.

12. The method of claim 10, further comprising directing the beam of an IR laser at the sample and alternating a pulse of the UV laser with a pulse of the IR laser.

13. The method of claim 10, wherein the sample comprises one or more of blood, animal tissue, plant tissue, lipids, proteins, or biomolecules.

14. The method of claim 10, further comprising capturing the protonated sample molecules for analysis.

15. The method of claim 14, wherein the analysis is selected from mass spectrometry, DNA sequencing, protein sequencing, or a combination thereof.

* * * * *

UNITED STATES PATENT AND TRADEMARK OFFICE
CERTIFICATE OF CORRECTION

PATENT NO. : 11,094,518 B2  
APPLICATION NO. : 16/891142  
DATED : August 17, 2021  
INVENTOR(S) : Kermit King Murray, Fabrizio Donnarumma and Oluwaremilekun Lawal Page 1 of 1

It is certified that error appears in the above-identified patent and that said Letters Patent is hereby corrected as shown below:

On the Title Page

Item (72) Inventor name delete "Lawai" and replace with --Lawal--

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*